US009669119B2

United States Patent
Amor et al.

(12) United States Patent
(10) Patent No.: US 9,669,119 B2
(45) Date of Patent: Jun. 6, 2017

(54) STERILIZER

(71) Applicant: AMERICAN STERILIZER COMPANY, Mentor, OH (US)

(72) Inventors: William Amor, Chagrin Falls, OH (US); Michael A. Bacik, Fairview, PA (US); Michael W. Butler, Highland Heights, OH (US); J. D. Cunningham, Apex, NC (US); Evan Kessick, Willoughby Hills, OH (US)

(73) Assignee: AMERICAN STERILIZER COMPANY, Mentor, OH (US)

( * ) Notice: Subject to any disclaimer, the term of this patent is extended or adjusted under 35 U.S.C. 154(b) by 0 days.

(21) Appl. No.: 14/704,056

(22) Filed: May 5, 2015

(65) Prior Publication Data

US 2015/0320896 A1    Nov. 12, 2015

Related U.S. Application Data

(60) Provisional application No. 61/989,187, filed on May 6, 2014.

(51) Int. Cl.
*A61L 2/07* (2006.01)
*A61B 50/30* (2016.01)
*A61B 50/00* (2016.01)

(52) U.S. Cl.
CPC ............... *A61L 2/07* (2013.01); *A61B 50/30* (2016.02); *A61B 2050/006* (2016.02);
(Continued)

(58) Field of Classification Search
CPC ... A61L 2/07; A61L 9/00; A61B 50/30; A61B 50/33
See application file for complete search history.

(56) References Cited

U.S. PATENT DOCUMENTS 3,351,422 A * 11/1967 Jones ................. A61L 2/24
219/480
4,085,668 A * 4/1978 Mughannam ............ A23L 3/10
99/359
(Continued)

FOREIGN PATENT DOCUMENTS

EP          0429960 B1    5/1995    ............... A61L 2/24

OTHER PUBLICATIONS

International Search Report issued in corresponding International Patent Application No. PCT/US2015/029207, dated Jul. 24, 2015.
(Continued)

*Primary Examiner* — Regina M Yoo
(74) *Attorney, Agent, or Firm* — Kusner & Jaffe; Michael A. Centanni

(57) ABSTRACT

A sterilizer for sterilizing medical instruments, the sterilizer having a pressurizable chamber having an opening communicating therewith. A door is provided for closing and sealing the opening to the chamber. A sterilant inlet and a sterilant outlet communicate with the chamber. A container holds medical instruments to be sterilized.

The container is comprised of a tray and a lid dimensioned to rest on the tray. The tray and lid define an interior area for holding medical instruments. The tray has connection means for connecting the sterilant inlet to the interior area of the tray when the tray is inserted in the chamber, and the lid is movable from the tray when pressurized sterilant is introduced into the cavity.

20 Claims, 18 Drawing Sheets

(52) U.S. Cl.
CPC . *A61B 2050/3011* (2016.02); *A61L 2202/122* (2013.01); *A61L 2202/14* (2013.01); *A61L 2202/17* (2013.01); *A61L 2202/24* (2013.01)

(56) References Cited

U.S. PATENT DOCUMENTS

| | | | | |
|---|---|---|---|---|
| 4,164,590 A | * | 8/1979 | Mencacci | A61L 2/04 426/407 |
| 4,798,292 A | * | 1/1989 | Hauze | A61L 2/26 206/210 |
| 5,223,229 A | * | 6/1993 | Brucker | A61L 2/07 292/36 |
| 5,266,275 A | * | 11/1993 | Faddis | A61L 2/202 422/116 |
| 5,313,738 A | | 5/1994 | Thakur et al. | 49/394 |
| 6,116,452 A | * | 9/2000 | Hamel | A61L 2/26 206/370 |
| 6,270,673 B1 | * | 8/2001 | Belt | A61M 1/30 210/646 |
| 6,759,017 B2 | | 7/2004 | Wu et al. | 422/300 |
| 7,169,369 B2 | | 1/2007 | Selig et al. | 422/292 |
| 7,303,734 B2 | * | 12/2007 | Moriyama | A61L 2/07 134/170 |
| 7,341,148 B2 | * | 3/2008 | Bettenhausen | A61L 2/18 206/370 |
| 7,608,228 B2 | * | 10/2009 | Horacek | A61L 2/04 422/292 |
| 7,905,353 B2 | * | 3/2011 | Baker | B65D 1/28 206/370 |
| 8,585,832 B2 | | 11/2013 | Lin et al. | 134/57 R |
| 2004/0197248 A1 | * | 10/2004 | Hasegawa | A61L 2/022 422/297 |
| 2005/0224493 A1 | | 10/2005 | Varma | 219/679 |
| 2008/0267817 A1 | * | 10/2008 | Coyle | A61L 2/07 422/26 |
| 2010/0224224 A1 | * | 9/2010 | Lin | A61L 2/07 134/57 R |
| 2011/0262301 A1 | * | 10/2011 | Ghelman | A61L 2/07 422/26 |
| 2012/0082589 A1 | | 4/2012 | Ladison et al. | 422/26 |
| 2014/0050634 A1 | | 2/2014 | Bacik et al. | 422/297 |

OTHER PUBLICATIONS

Barnstead New Chemiclave Sterilizers, published online, Nov. 10, 2016 (http://www.sterilizers.com/barnstead-chemicalave-sterilizers.asp).

* cited by examiner

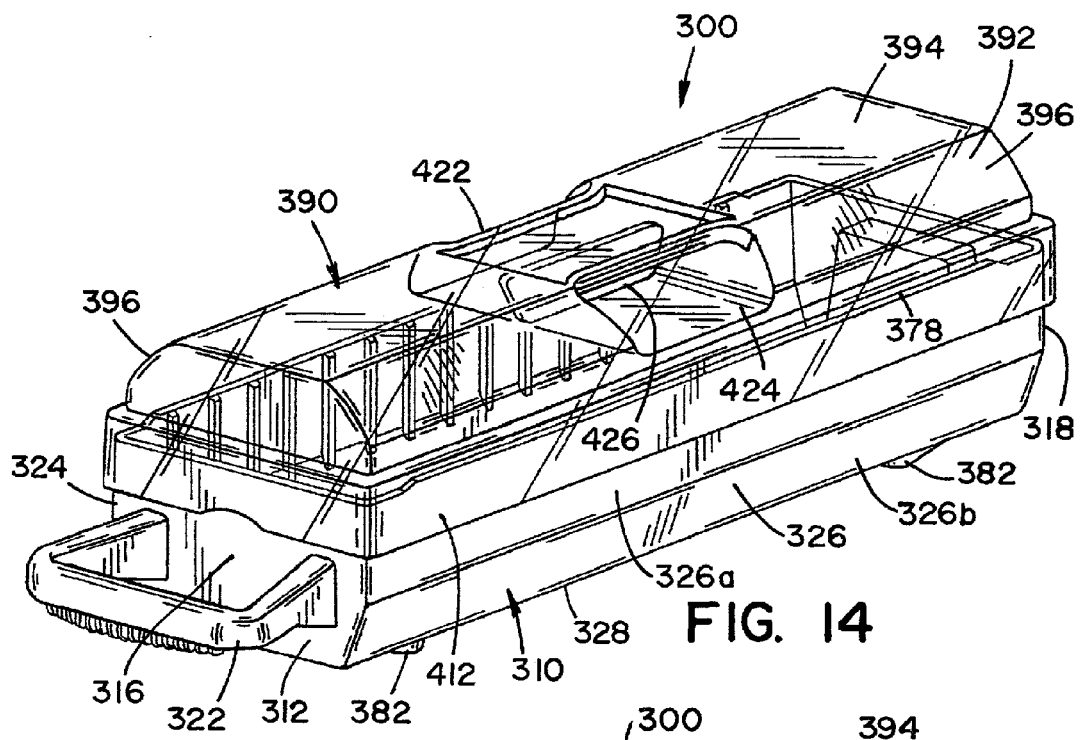
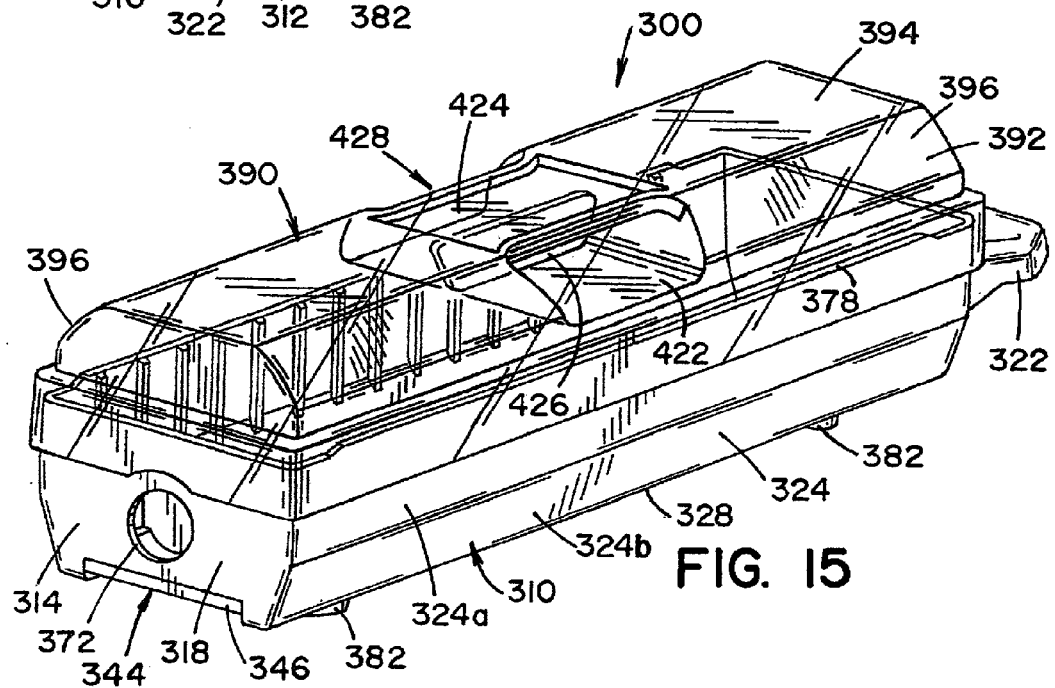

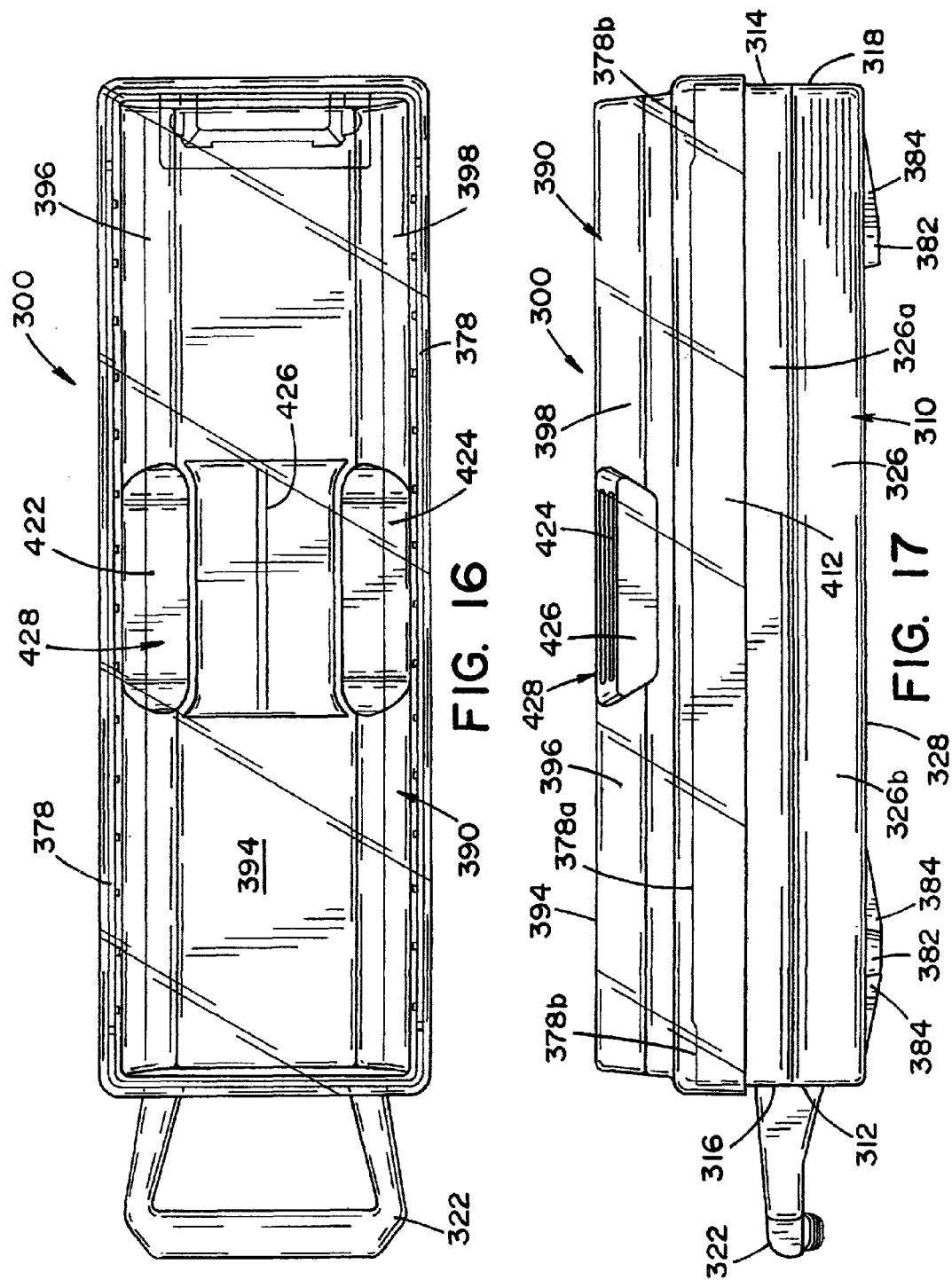

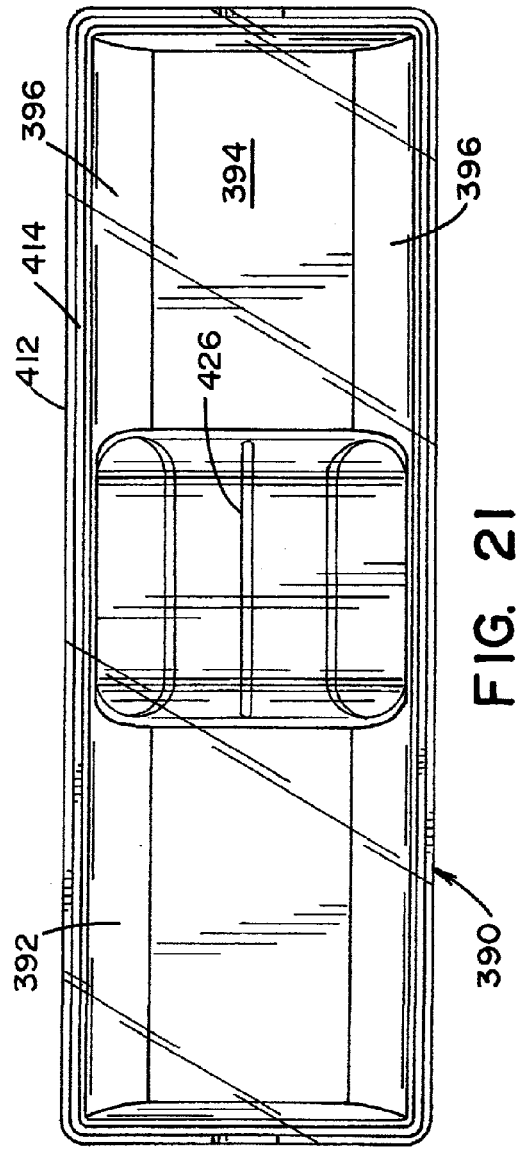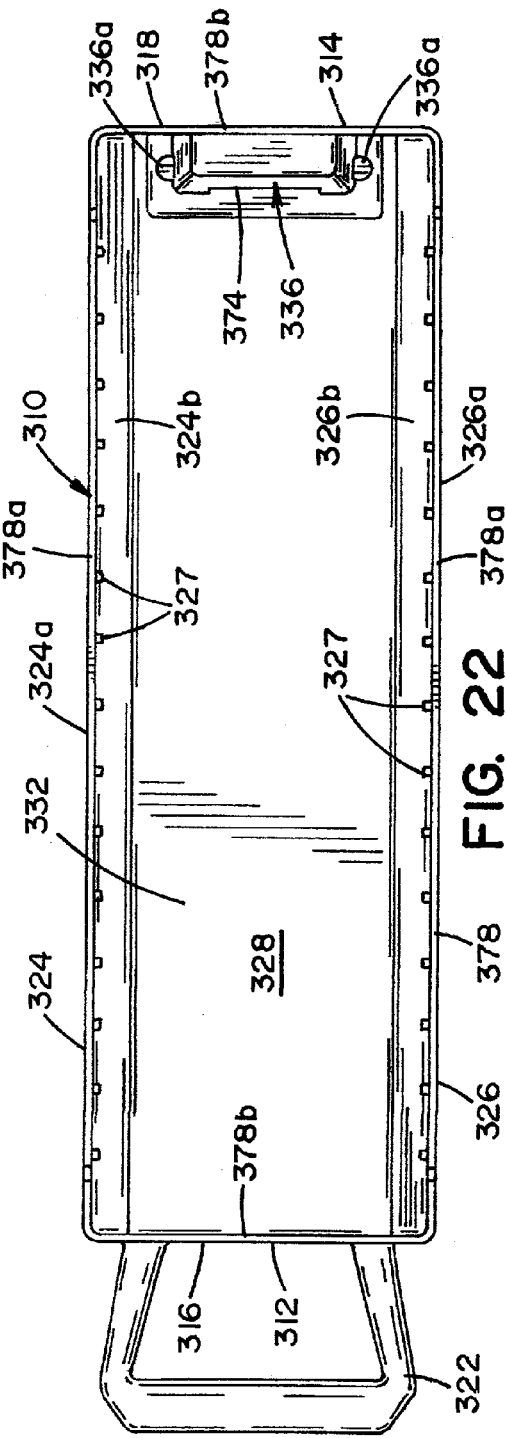

STERILIZER

RELATED APPLICATIONS

This application claims the benefit of U.S. Provisional Application No. 61/989,187, filed on May 6, 2014, which is fully incorporated herein by reference.

FIELD OF THE INVENTION

The present invention relates to disinfection or deactivation of medical, dental, pharmaceutical, veterinary or mortuary instruments and devices and, more particularly, to a method and apparatus for deactivating items and for maintaining the items in a deactivated state.

BACKGROUND OF THE INVENTION

Medical, dental, pharmaceutical, veterinary or mortuary instruments and devices that are exposed to blood or other body fluids require thorough cleaning and anti-microbial deactivation between each use. It is not unusual during a medical procedure for a medical device that is being used during the procedure to require immediate cleaning, i.e., sterilization, to allow continued use of the device. For example, a medical device may be dropped to the floor or may come in contact with a non-sterile surface. Either situation would require sterilization of the instrument or device before further use. Sterilization processes that provide quick turnaround have historically been referred to as "flash" sterilization. More recently, the term "immediate use" sterilization is considered more appropriate.

The present invention provides a sterilizer for "immediate use" sterilization, which sterilizer provides a container that maintains the sterilized device sterile during transport from the sterilizer to a surgical suite or other area of use.

SUMMARY OF THE INVENTION

In accordance with the present invention, there is provided a sterilizer for sterilizing medical instruments. The sterilizer is comprised of a pressure vessel having an opening communicating with an interior cavity and a door assembly for closing and sealing the opening to the cavity. A sterilant inlet and a sterilant outlet communicate with the chamber. A container for holding medical instruments to be sterilized is provided. The container is comprised of a tray and a lid dimensioned to rest on the tray. The tray and lid define an interior area for holding medical instruments. The tray has connection means for connecting the sterilant inlet to the interior area of the tray when the tray is inserted in the cavity. The lid is movable from the tray when pressurized sterilant is introduced into the interior area of the container, the sterilant flowing past the lid to the sterilant outlet.

One advantage of the present invention is the provision of a sterilizer for deactivating/sterilizing medical instruments and items.

Another advantage of the present invention is a sterilizer as described above that deactivates medical instruments and items using steam.

Another advantage of the present invention is a sterilizer as described above wherein the medical instruments are deactivated in a container comprised of a tray and a removable lid.

A still further advantage of the present invention is a sterilizer as described above wherein the interior and exterior of the container are exposed to steam within an enclosed sterilization chamber.

A still further advantage of the present invention is a sterilizer as described above that includes a door assembly that allows insertion and removal of the container into and out of the sterilization chamber.

A still further advantage of the present invention is a sterilizer as described above wherein the door assembly has a recessed cavity that forms part of the sterilization chamber.

A still further advantage of the present invention is a sterilizer as described above wherein the recessed cavity of the door assembly is dimensioned to receive the extending portion of the container.

A still further advantage of the present invention is a sterilizer as described above wherein the portion of the container that extends from the sterilization chamber is in the form of a handle that allows the user to grip the container.

A still further advantage of the present invention is a sterilizer as described above wherein the lid of the container is dimensioned to rest on the tray and is movable from the tray when steam is introduced into the container.

A still further advantage of the present invention is a sterilizer as described above wherein the door assembly includes a thermal insulating inner lining having a recessed area.

A still further advantage of the present invention is a sterilizer as described above wherein the inner lining of the door assembly has a lower portion dimensioned to direct condensate toward a drain when the door is in a closed position.

Another advantage of the present invention is the provision of a container for holding medical instruments and items during a sterilization process, which container maintains the instruments in a sterile environment during transfer from the sterilizer to a work environment.

A still further advantage of the present invention is a container as described above that may be used to transport sterilized instruments in a sterile environment from the sterilizer to a working location.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 14 is a top, front perspective view of a container for holding medical instruments, which container is used in the sterilizer;

FIG. 15 is a top, back perspective view of the container shown in FIG. 14;

FIG. 16 is a top, plan view of the container;

FIG. 17 is a first side view of the container;

FIG. 21 is a bottom view of a lid that forms part of the container;

FIG. 22 is a top plan view of a tray that forms part of the container;

DETAILED DESCRIPTION OF PREFERRED EMBODIMENT

Figure 1:
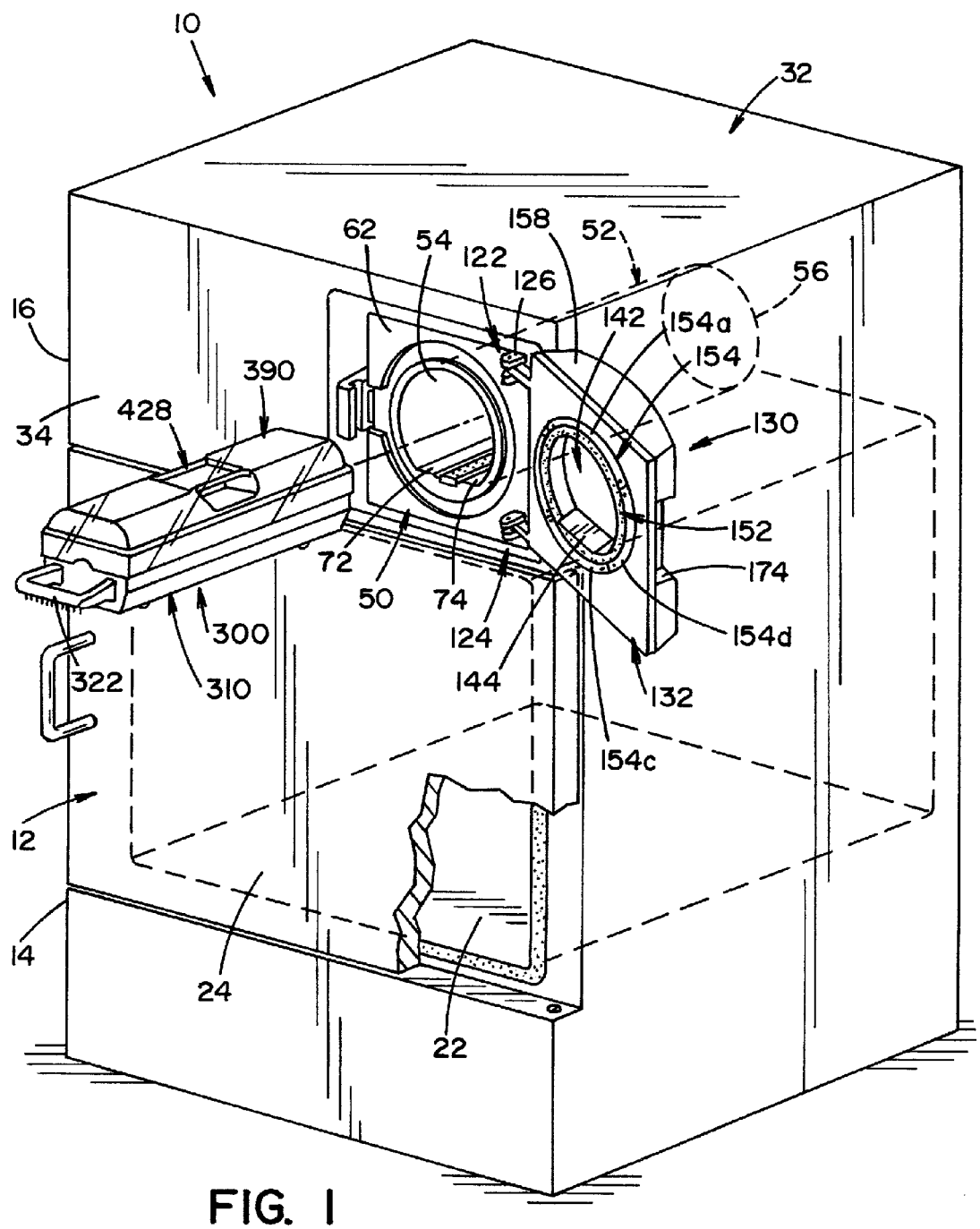
FIG. 1 is a perspective view of a decontamination system including an immediate-use sterilizer, illustrating a preferred embodiment of the present invention.

Referring now to the drawings wherein the showings are for the purpose of illustrating a preferred embodiment of the invention only and not for the purpose of limiting same, FIG. 1 is a perspective view of a decontamination system 10 having an immediate-use sterilizer 50 according to the present invention forming a part thereof. In the embodiment shown, decontamination system 10 includes a large conventional decontamination apparatus 12 on a lower portion 14 of decontamination system 10 and immediate-use sterilizer 50, according to the present invention, located in an upper portion 16 of the decontamination system 10. In the embodiment shown, decontamination apparatus 12 includes a large decontamination chamber 22 that is accessible by a hinged door 24. Large decontamination apparatus 12 would typically be used for decontaminating large loads of instruments in a conventionally known manner.

Immediate-use sterilizer 50 is designed for quick sterilization/decontamination of a small load of medical instruments and other devices. In the embodiment shown, sterilizer 50 is disposed within housing structure 32 of decontamination system 10. As will be appreciated from a further reading of the specification, sterilizer 50 could be separate from decontamination system 10 and could be contained in a separate, smaller housing.

Sterilizer 50 includes a pressure vessel 52 that is disposed within housing structure 32 of decontamination system 10. Pressure vessel 52 has an open end 54 that communicates with an opening through a front panel 34 of the housing structure 32. (In this specification, open end 54 of pressure vessel 52 may also be referred to as the front end 54 of pressure vessel 52.) Pressure vessel 52 has a rounded, contoured closed end 56.

Figure 2:
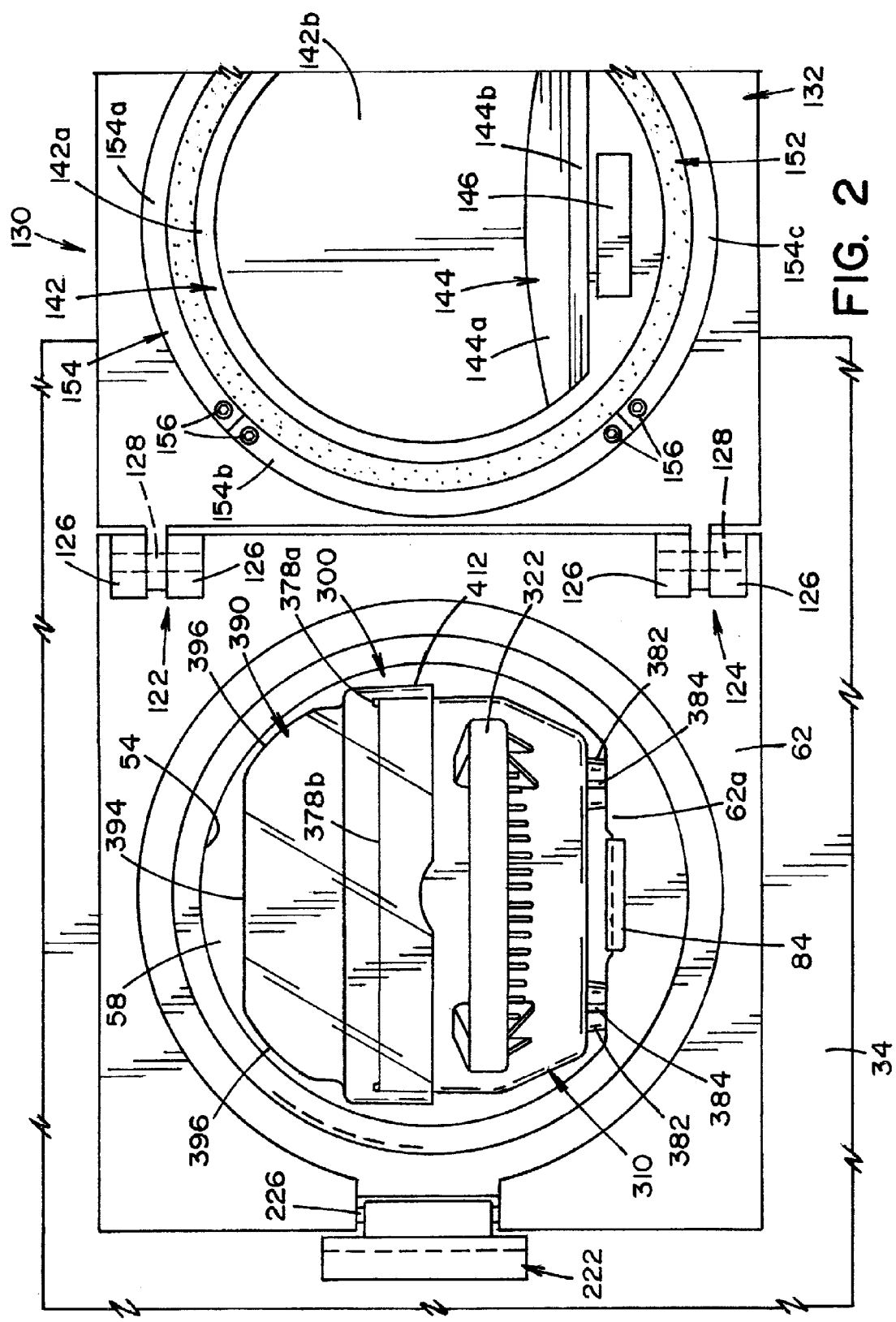
FIG. 2 is a front view of the immediate-use sterilizer of FIG. 1, showing a container within the sterilizer and a door assembly in an open position.
Figure 5:
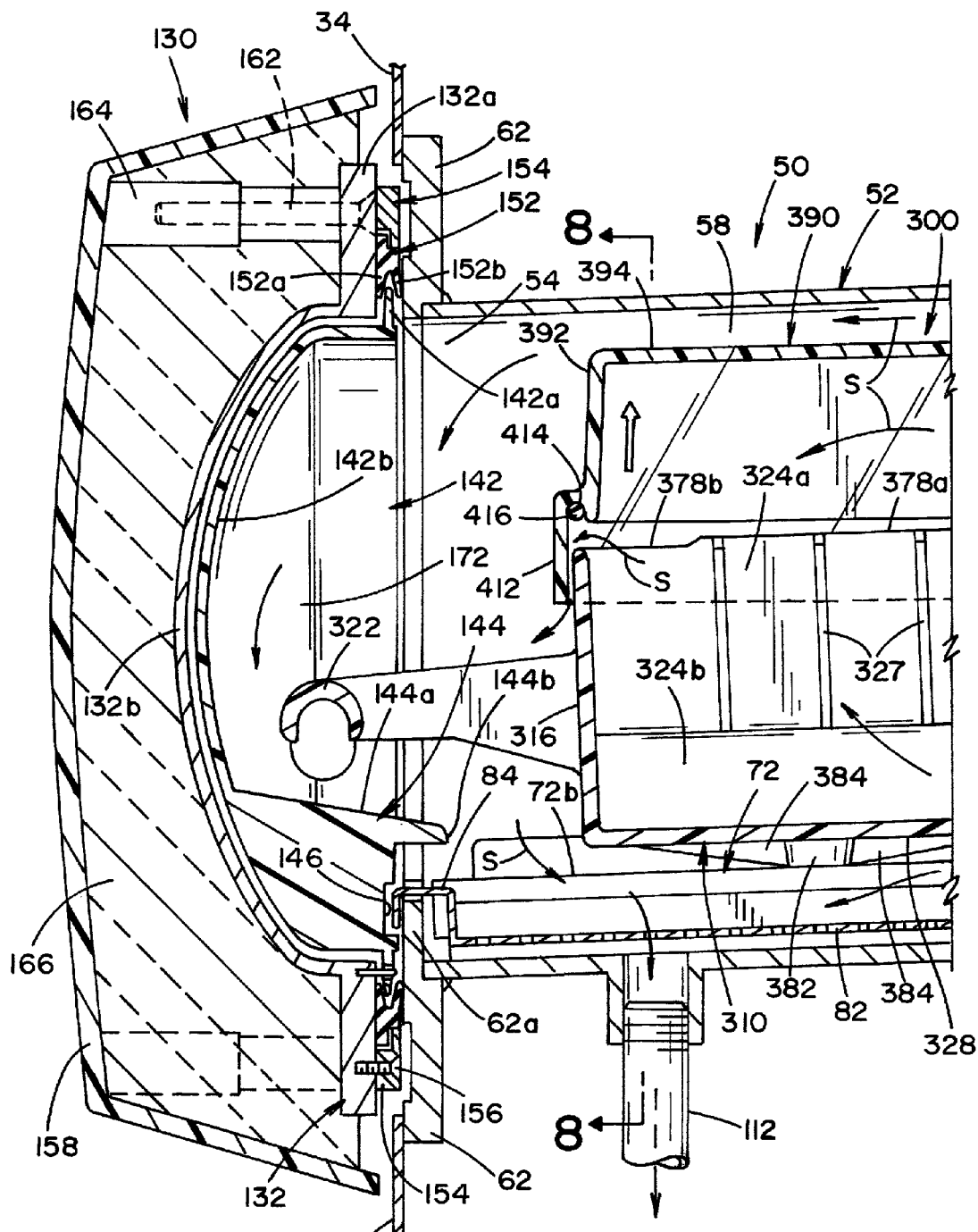
FIG. 5 is an enlarged, cross-sectional view of the front end of the sterilizer, showing a container within the sterilizer and a door assembly in a closed position.

Pressure vessel 52 is preferably formed of a metal material, such as, by way of example and not limitation, stainless steel, and is dimensioned to be able to withstand pressures up to about 100 psi, as shall be described in greater detail below. As shown in the drawings, pressure vessel 52 is elongated and generally cylindrical in shape and defines a generally cylindrical inner cavity 58. Inner cavity 58 is accessible through an opening in the front panel 34 of housing 32. A flange 62 surrounds and extends outwardly from open end 54 of pressure vessel 52. Flange 62 is comprised of a rigid metal plate fixedly secured, preferably by welding, to the open end 54 of the pressure vessel. Flange 62 is secured to front end 54 of pressure vessel 52 to form a fluid tight and pressure-tight seal therewith. Flange 62 includes a short wall 62a that traverses a lower portion of the opening in pressure vessel 52, as best seen in FIGS. 2 and 5. In this respect, short wall portion 62a of flange 62 basically forms a dam or weir at front end 54 of pressure vessel 52. Pressure vessel 52 is oriented at a slight angle relative to flange 62. In other words, pressure vessel 52 is inclined relative to flange 62 and front panel 34 of housing 32, wherein pressure vessel 52 slopes slightly downwardly from closed back end 56 toward opened front end 54.

Figure 10:
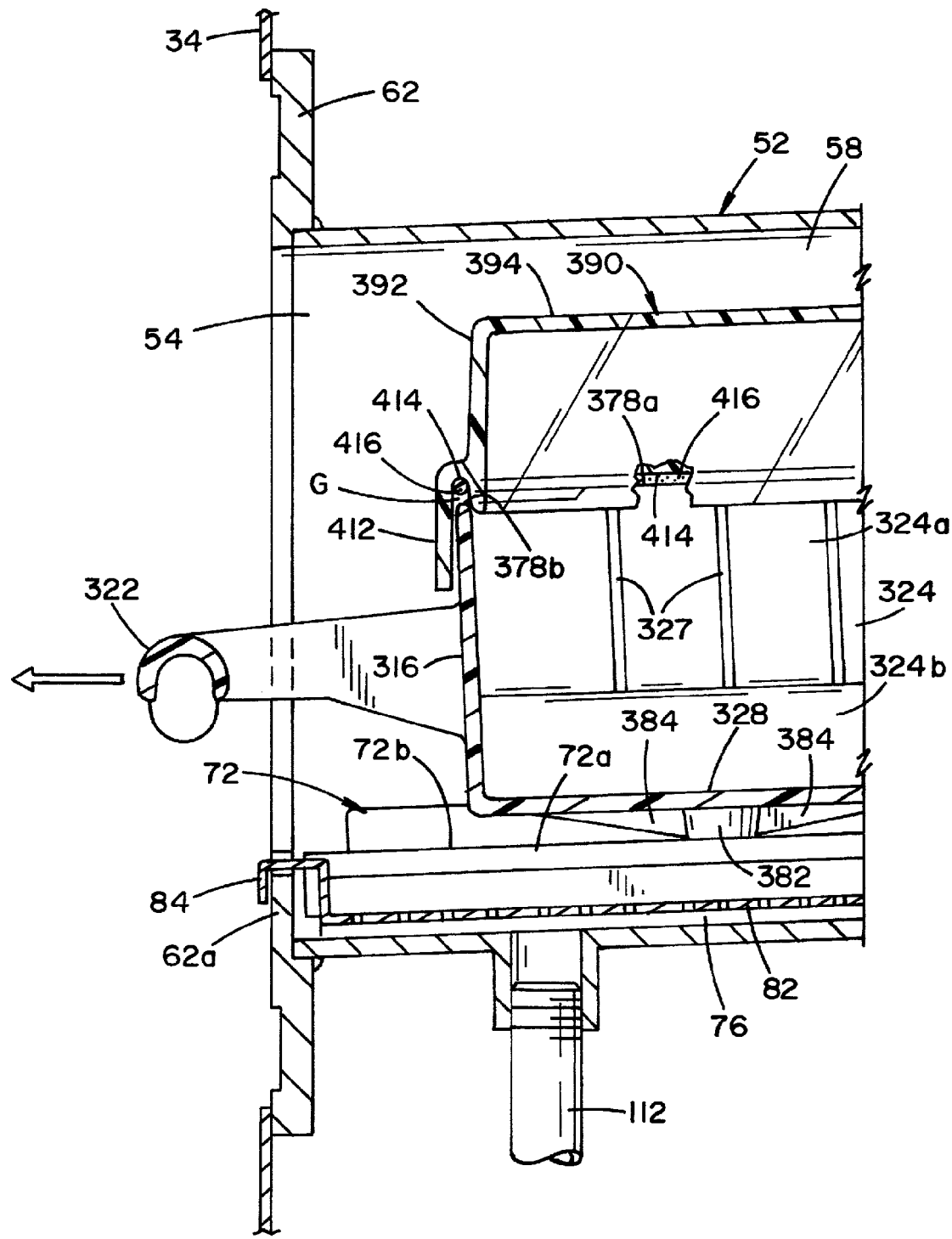
FIG. 10 is an enlarged, cross-sectional view of the front end of the sterilizer, illustrating how the container is accessible for removal from the sterilizer.

A pair of spaced-apart rails 72, 74 is provided along the inner surface of pressure vessel 52. Rails 72, 74 are disposed near the bottom of inner cavity 58 and extend along the length of pressure vessel 52. In the embodiment shown, rails 72, 74 are preferably formed of the same metal used to form pressure vessel 52. Rails 72, 74 are preferably attached to the inner surface of pressure vessel 52 by welding Inner edges 72a, 74a of rails 72, 74 define a channel 76 therebetween. Each rail 72, 74 defines an elongated, upward-facing flat surface 72b, 74b that extends along the length of inner cavity 58 of pressure vessel 52. Flat surfaces 72b, 74b of rails 72, 74 are coplanar to each other and define a support surface for supporting a container 300, as shall be defined in greater detail below. A strainer 82 is provided in channel 76 that is defined between inner edges 72a, 74a of rails 72, 74. Strainer 82 is provided to screen or filter solid particulate from condensate formed in inner cavity 58 during a sterilization cycle, as shall be described in greater detail below. Strainer 82 extends from closed, back end 56 of pressure vessel 52 to short wall 62a of flange 62 that extends across open, front end 54 of pressure vessel 52. A U-shaped clip 84 is attached to a front end of strainer 82 to attach onto short wall 62a of flange 62, as best seen in FIG. 10, to facilitate positioning and removal of strainer 82.

Figure 3:
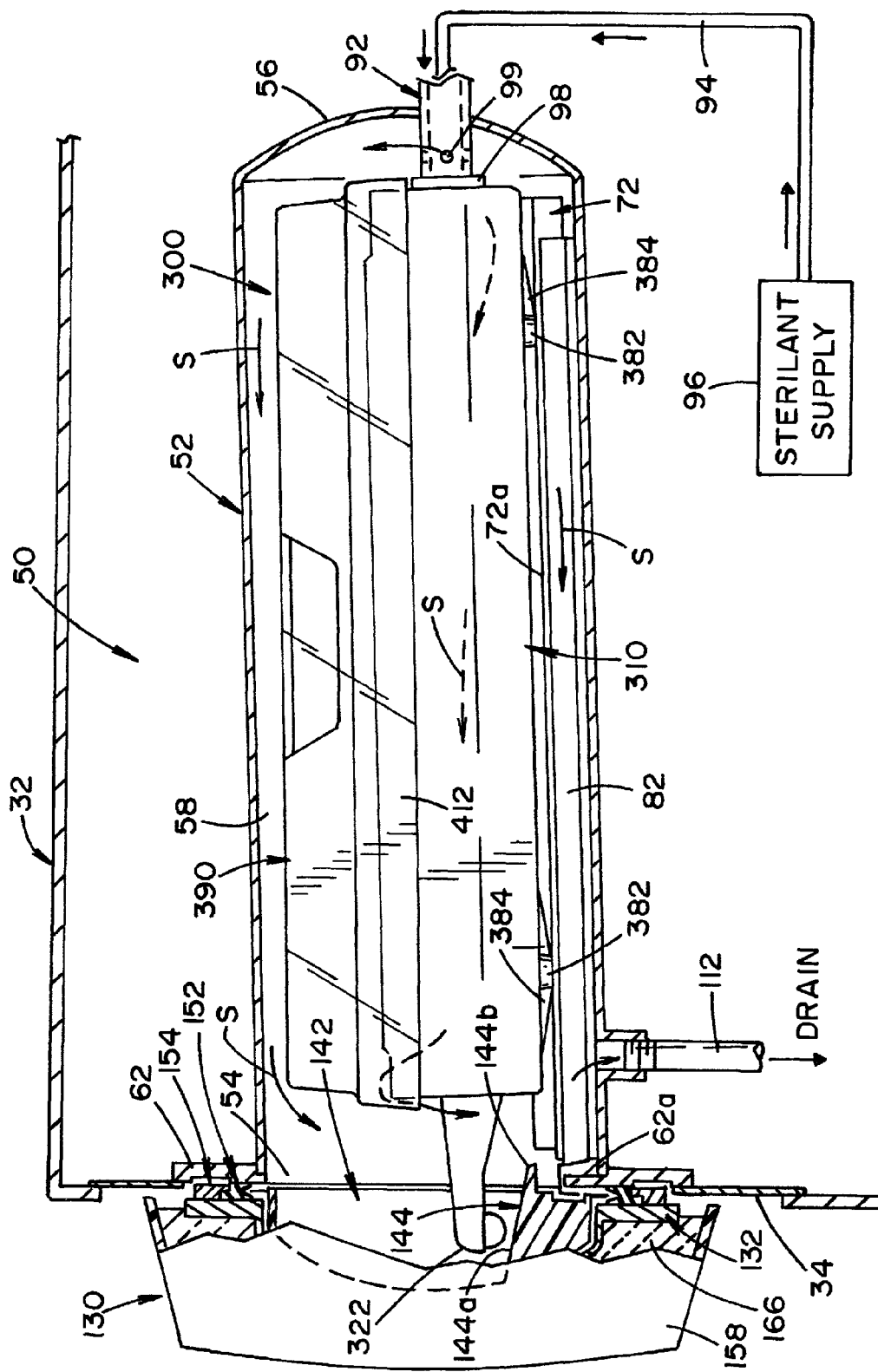
FIG. 3 is a cross-sectional view of the immediate-use sterilizer shown in FIG. 1.
Figure 4:
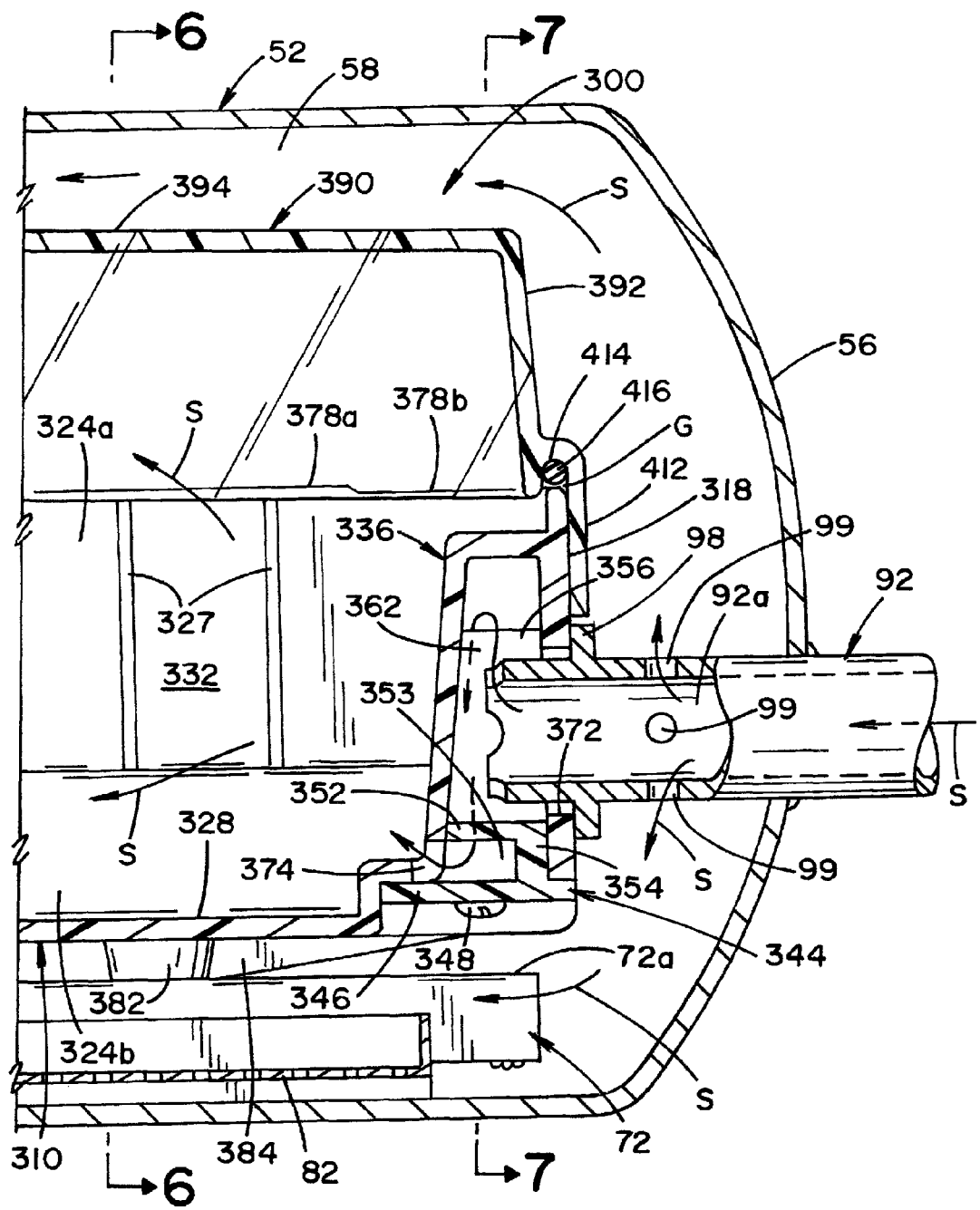
FIG. 4 is an enlarged, cross-sectional view of a back end or closed end of the sterilizer, showing a container connected to an inlet connector.

Referring now to FIGS. 3 and 4, an elongated connector 92 extends into inner cavity 58 of pressure vessel 52 through closed, back end 56 of pressure vessel 52. In the embodiment shown, connector 92 is tubular in shape and extends generally parallel to the axis of pressure vessel 52. Connector 92 defines an inner passageway 92a that communicates with a sterilant inlet line 94. Sterilant inlet line 94 is connected to a sterilant source 96, schematically illustrated in FIG. 3. Sterilant inlet line 94 communicates with inner cavity 58 of pressure vessel 52 through connector 92. Connector 92 has an annular flange 98 extending outwardly from the outer surface thereof. Flange 98 is spaced a predetermined distance from the free, open end of connector 92. Radially oriented openings 99 extend through connector 92 and communicate with passage 92a through connector 92. Openings 99 are located between flange 98 and closed, back end 56 of pressure vessel 52 at a location where connector 92 extends from closed, back end 56 of pressure vessel 52. In a preferred embodiment of the invention, the sterilant used to sterilize the articles in pressure vessel 52 is steam. The steam may be provided by a steam generator or may be obtained from an external source. The steam, preferably, would have an operating pressure between 50-80 psi and have a quality range of between 97% to 100% and a temperature range between 297° F. and 325° F.

A sterilant outlet 112 is provided and is disposed near open, front end 54 of pressure vessel 52 at the bottom thereof. In a preferred embodiment, where steam is used as the sterilizing agent, sterilant outlet 112 is essentially the drain operable to drain water, condensate, and residual steam from pressure vessel 52. A pressure relief line (not shown) is connected to pressure vessel 52 to relieve pressure within pressure vessel 52.

A system microprocessor or microcontroller (not shown) controls the operation of the inlet and outlet lines 94, 112. In this respect, valves (not shown) controlling the flow of pressure or access to drain line 112 from pressure vessel 52 would be controlled by the controller.

Two pairs 122, 124 of spaced-apart lugs 126 extend from a front face of flange 62, as best seen in FIGS. 1 and 2. Lugs 126 are disposed to one side of the opening in pressure vessel 52 to support a door assembly 130 for opening and closing access to inner cavity 58 of pressure vessel 52. Aligned openings extend through pairs 122, 124 of spaced-apart lugs 126. The openings in lugs 126 are dimensioned to receive pivot pins 128 for supporting door assembly 130.

Door assembly 130 is comprised of a door plate 132 that includes a generally flat, rectangular section 132a and a dome section 132b. In the embodiment shown, flat section 132a and dome section 132b are integrally formed of metal. It is also contemplated that flat section 132a and dome section 132b could each be separate components that are welded together to form a pressure-type, fluid-type weld therebetween. Dome section 132b of door assembly 130 defines a concave recess that is dimensioned to correspond to the shape, i.e., diameter, of inner cavity 58 of pressure vessel 52. Door assembly 130 further includes an inner liner 142, best seen in FIG. 9, that is formed of an insulating material, preferably a polymer Inner liner 142 is dimensioned to closely match the shape of the inner surface of dome section 132b of door plate 132. Inner liner 142 includes an annular flat flange section 142a and a dome section 142b extending outwardly and generally parallel to flat section 132a of door plate 132. Dome section 142b of inner liner 142 is dimensioned to closely fit within the recessed area defined by dome section 132b of door plate 132.

Figure 9:
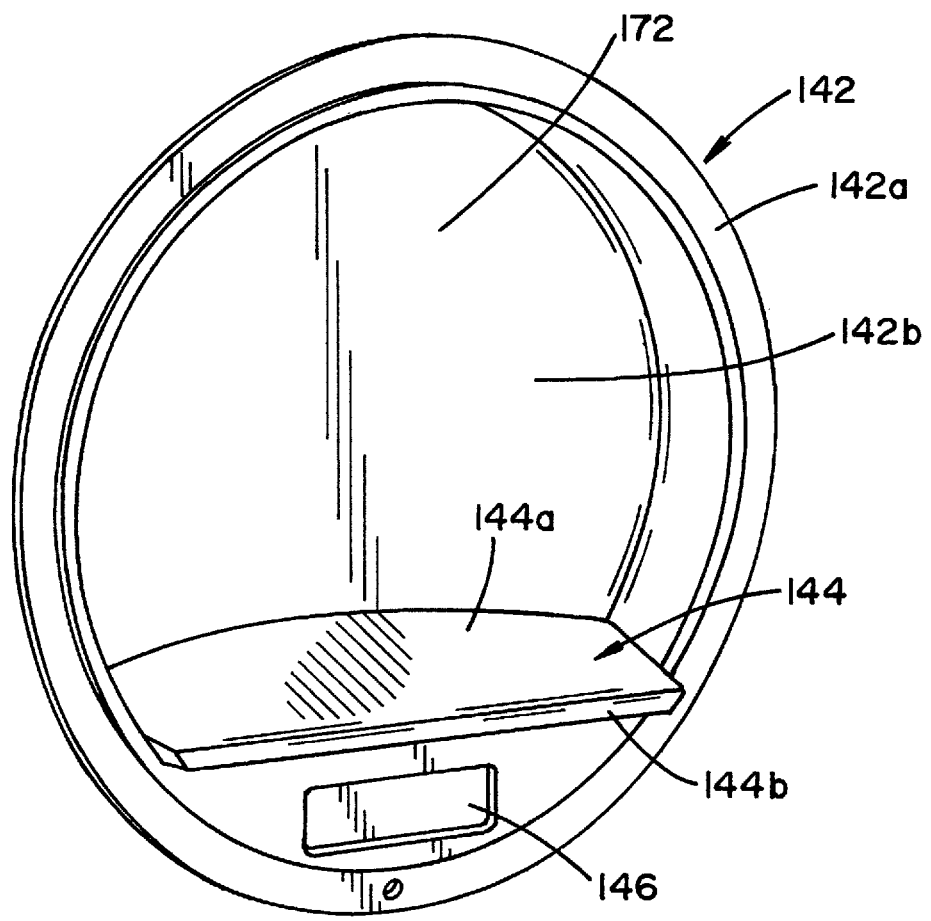
FIG. 9 is a perspective view of an insulating liner that forms part of the door assembly.

As best seen in FIG. 9, inner liner 142 of door assembly 130 is molded or otherwise formed to have a ledge or shelf 144 on the lower portion thereof. Shelf 144 has an upward-facing, downward-sloping surface 144a that terminates in an edge 144b. Surface 144a of shelf 144 slopes toward pressure vessel 52 and is dimensioned to extend into inner cavity 58 of pressure vessel 52, when door assembly 130 is in a closed position. A rectangular recess 146 is formed in inner liner 142 below shelf 144. Recess 146 is dimensioned to receive U-shaped clip 84 when door assembly 130 is in a closed position. Liner 142 defines a cup-shaped recess 172 above shelf 144, as best seen in FIG. 9.

An annular gasket 152 is mounted onto flange section 142a of inner liner 142. Gasket 152 is generally Y-shaped and has two leg portions 152a, 152b that are dimensioned to receive the outer edge of flange section 142a. A flat retainer ring 154, secured to door plate 132 by conventional fasteners 156, secures gasket 152 against door plate 132. In the embodiment shown, retainer ring 154 is comprised of a plurality of ring sections, designated 154a, 154b, 154c, etc. A door facade 158 is provided to cover door plate 132 of door assembly 130. In the embodiment shown, door facade 158 is a molded polymer structure dimensioned to be spaced from dome section 132b of metal door plate 132 of door assembly 130. Door facade 158 is mounted to door plate 132 by fasteners 162 that extend through holes in door plate 132 into mounting posts 164 that are formed and extend from the inner surface of door facade 158, as best seen in FIG. 5. Door facade 158 includes a notched-out area 174, best seen in FIG. 1, that exposes a portion of door plate 132. In the embodiment shown, an insulating material 166 is disposed in the space defined between door facade 158 and door plate 132.

Door assembly 130 is pivotally movable relative to opened, front end 54 of pressure vessel 52. Door assembly 130 is movable between an opened position, allowing access to inner cavity 58 of pressure vessel 52, and a closed position, closing access to the opening to pressure vessel 52.

In a closed position, dome portion 142b of inner liner 142 of door assembly 130 aligns with inner cavity 58 of pressure vessel 52. The cup-shaped recess 172 in inner liner 142 of door assembly 130 and cavity 58 within pressure vessel 52 together define a sterilization chamber when door assembly 130 is in the closed position.

Figure 11:
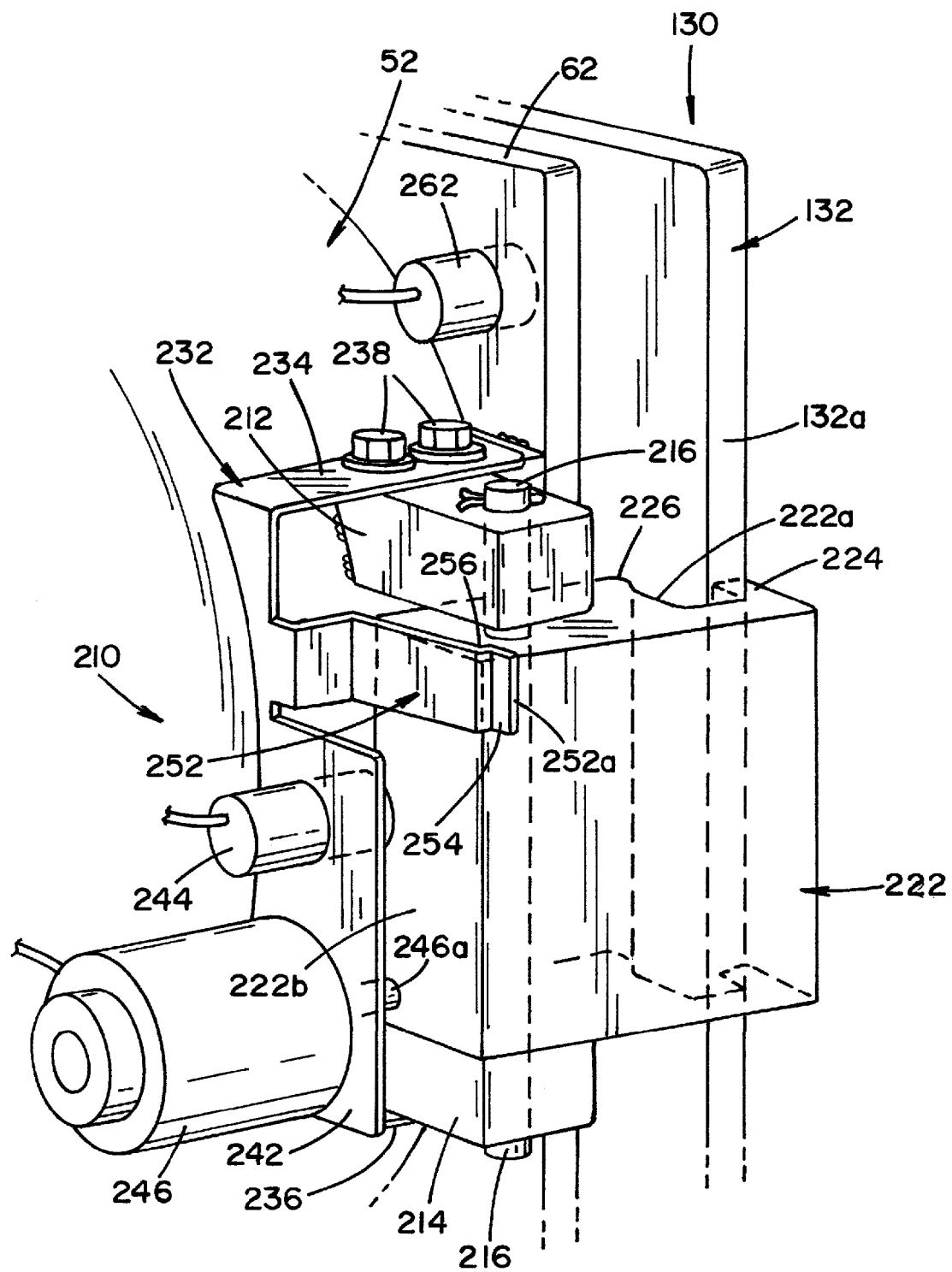
FIG. 11 is a perspective view of a latch assembly for securing and releasing the door assembly.
Figure 12:
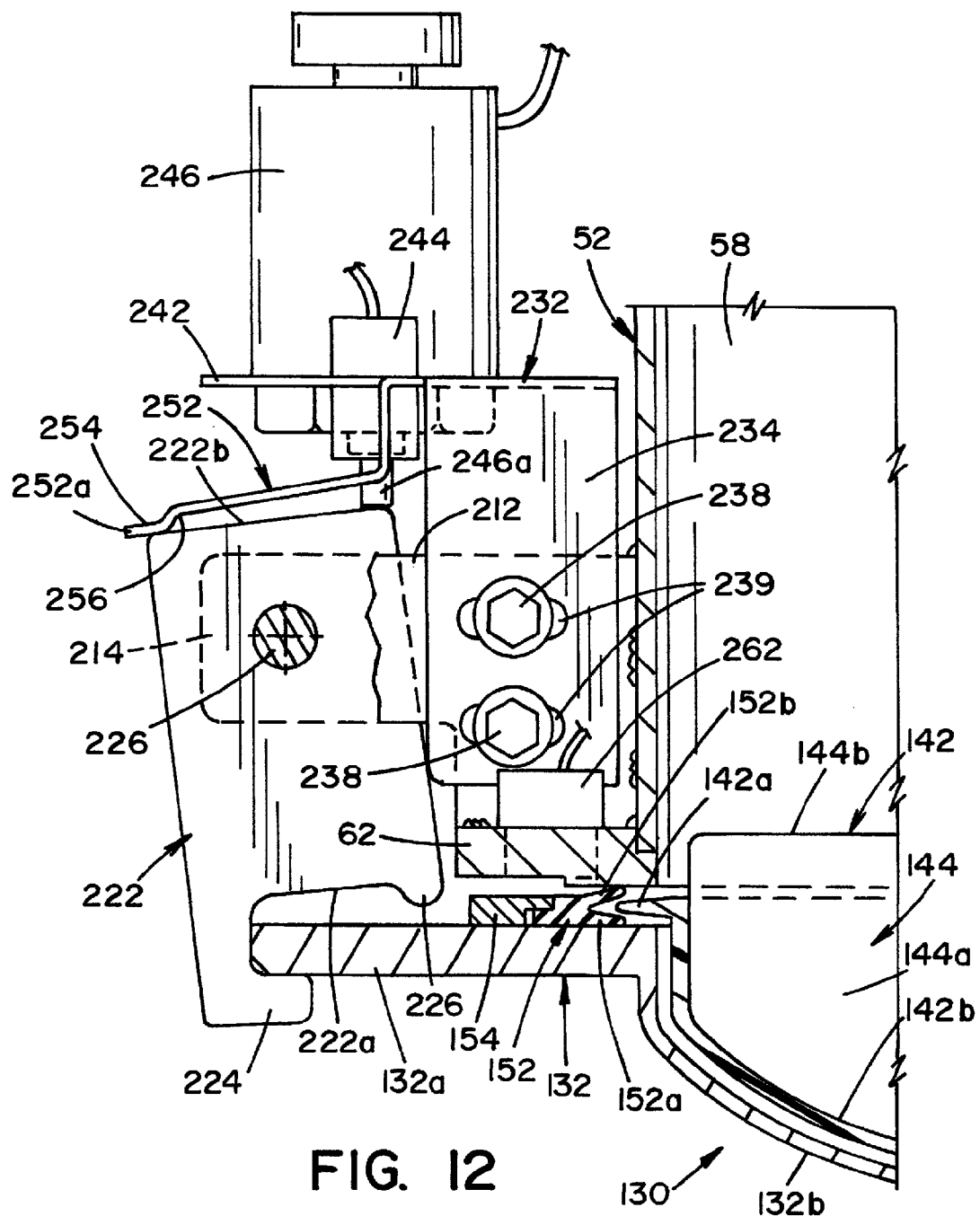
FIG. 12 is a top view of the latch assembly, showing the latch assembly securing the door assembly in a closed position.
Figure 13:
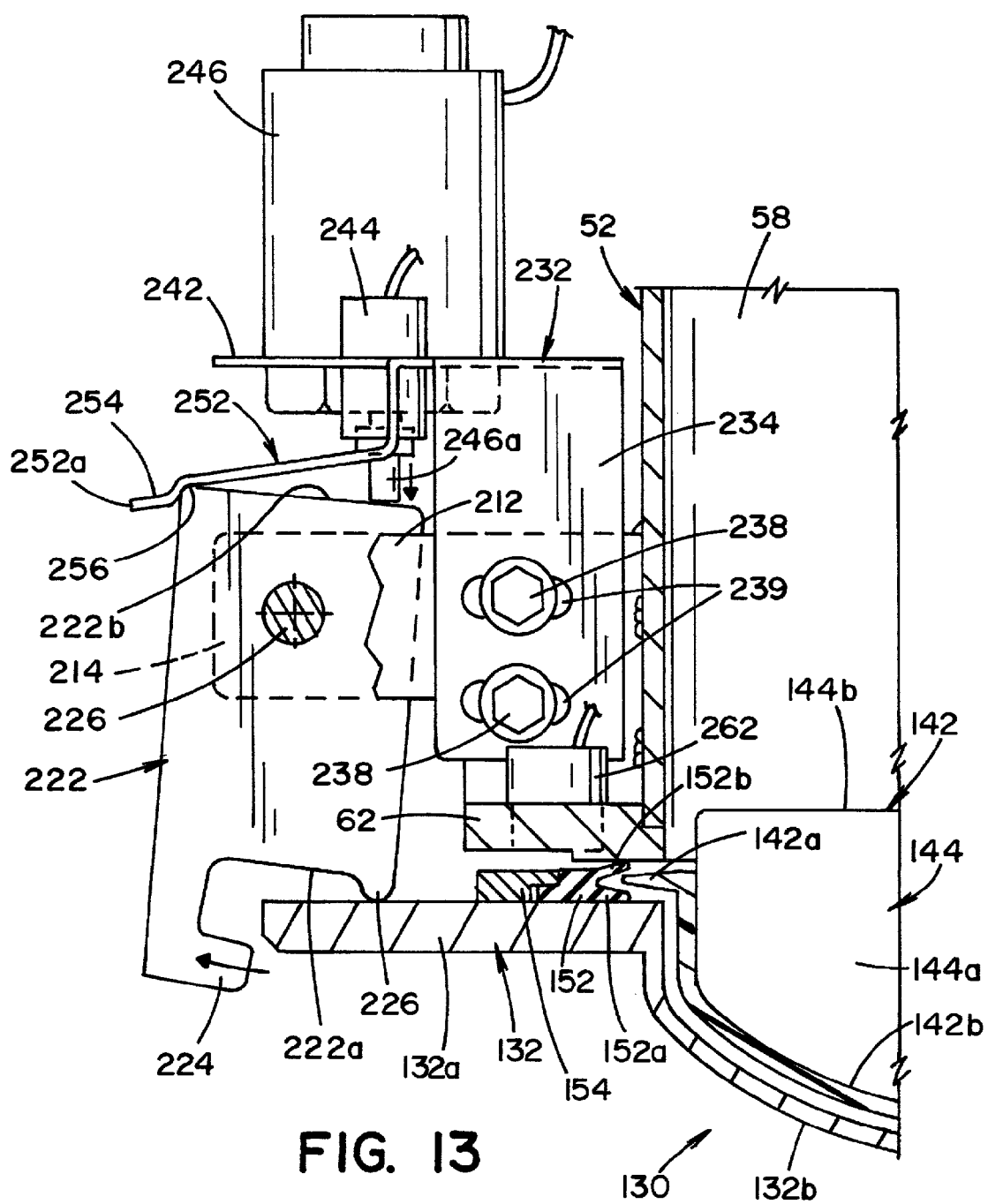
FIG. 13 is a top view of the latch assembly, showing the latch assembly releasing the door assembly.
Figure 18:
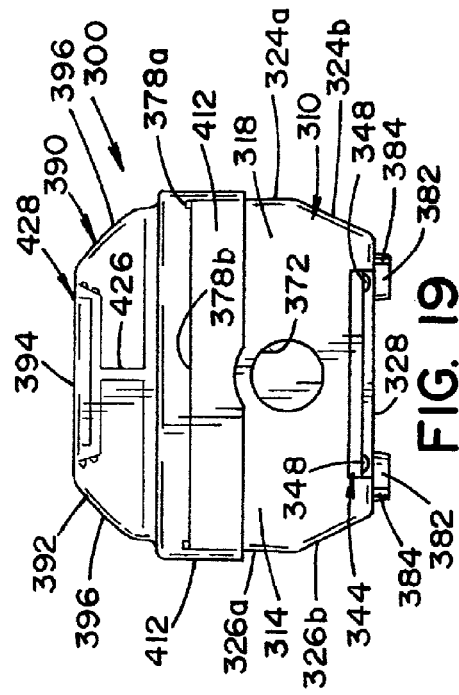
FIG. 18 is a front end view of the container.
Figure 19:
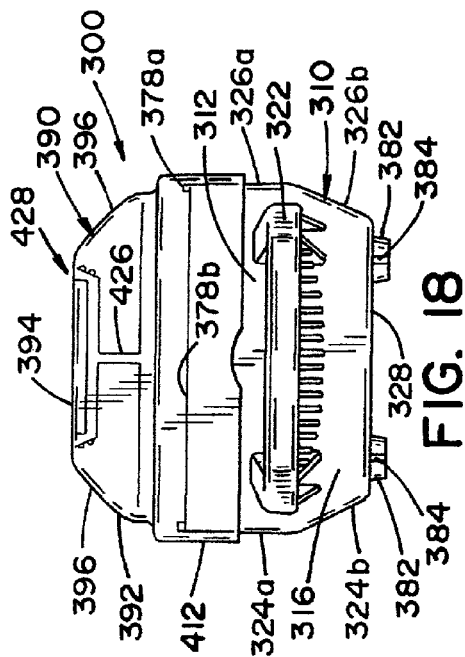
FIG. 19 is a back end view of the container.
Figure 20:
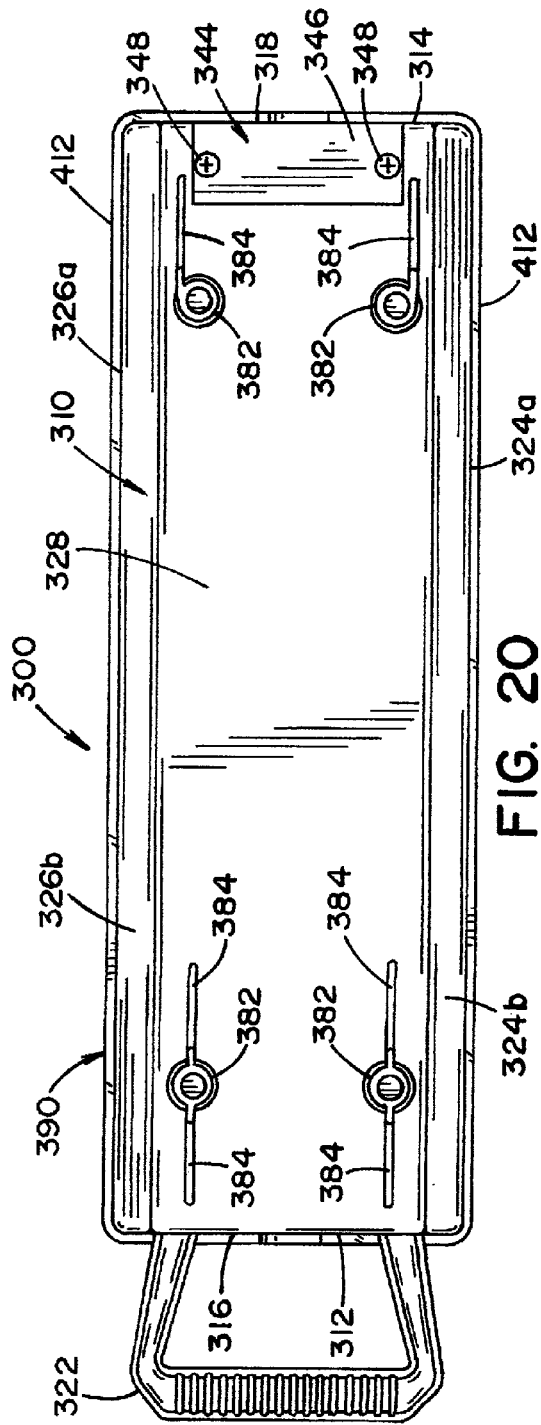
FIG. 20 is a bottom view of the container.
Figure 23:
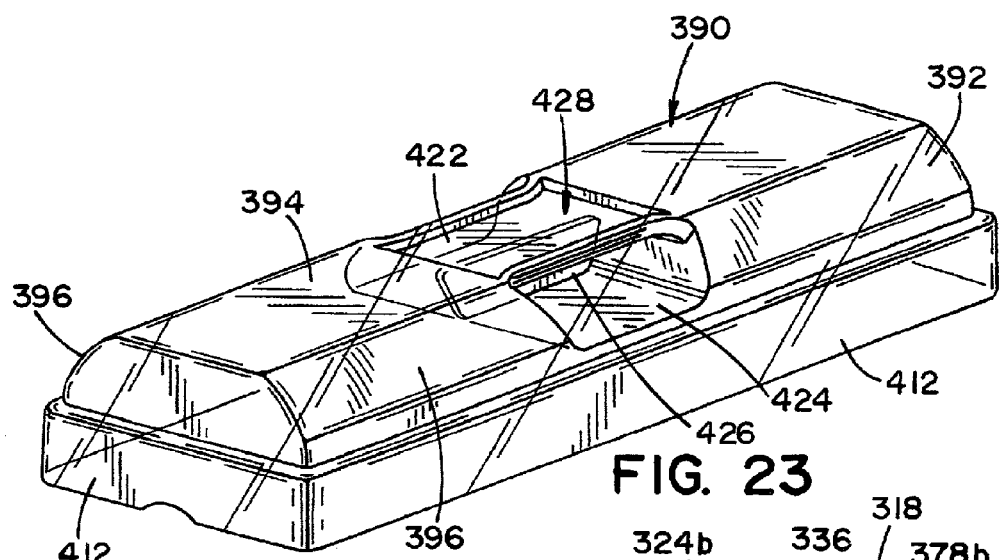
FIG. 23 is a perspective view of the lid of the container.
Figure 24:
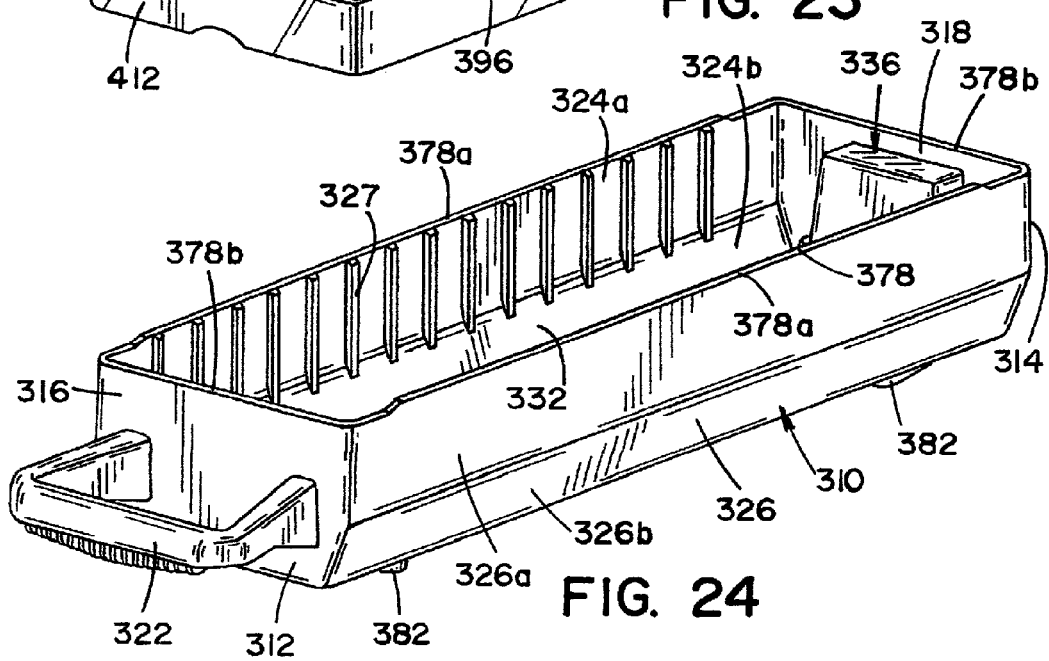
FIG. 24 is a perspective view of the tray of the container.

Referring now to FIGS. 11-13, a latch assembly 210 is best seen. Latch assembly 210 is provided to secure door assembly 130 to pressure vessel 52 when door assembly 130 is in the closed position. A pair of spaced-apart blocks 212, 214 is mounted to the exterior surface of pressure vessel 52. Blocks 212, 214 are disposed near the opening in pressure vessel 52 and extend from one side of pressure vessel 52. Vertically aligned openings extend through blocks 212, 214 and are dimensioned to support a pivot pin 216. Pivot pin 216 supports a pivotally movable latch element 222, as best seen in FIG. 11. Latch element 222 is generally rectangular in shape and has an L-shaped latching tab 224 extending from a front face 222a thereof. Latching tab 224 is dimensioned and positioned to capture a lateral edge of the exposed portion of door plate 132 of door assembly 130, as shall be described in greater detail below. A paw 226 extends from face 222a along one edge of latch element 222.

A bracket 232 having two spaced-apart arms 234, 236 is provided for attachment to blocks 212, 214. Arms 234, 236 are dimensioned and spaced apart to allow attachment of bracket 232 to outer surfaces of the blocks 212, 214, as shown in FIGS. 11-13. Conventional fasteners 238 extend through slotted holes 239 in arms 234, 236 to mount bracket 232 to blocks 212, 214. Bracket 232 further includes a mounting plate 242, spaced from a back surface 222b of latch element 222. Mounting plate 242 is provided to support a sensor element 244 to detect the position of latch element 222 and an actuator 246 device to operatively engage latch element 222, as shall be described in greater detail below. In the embodiment shown, sensor element 244 is a magnetic sensor and actuator 246 is a solenoid having a movable pin 246a.

Bracket 232 also includes a resilient biasing element 252 that is dimensioned to engage and bias latch element 222. In the embodiment shown, biasing element 252 is in the form of an elongated metallic strip having a free end 252a that is formed to define an offset tab portion 254 at free end 252a. Where offset tab portion 254 is formed, a recess or detent 256 is defined, as best seen in FIG. 12. Bracket 232 is preferably formed of a metallic material, such as steel, and is hardened such that biasing element 252 is a spring element. Biasing element 252 is dimensioned to engage latch element 222 in two different ways.

In a first position, detent 256 of biasing element 252 captures an edge or corner of latch element 222, as illustrated in FIG. 13, wherein the biasing force of biasing element 252 exerted against latch element 222 holds latch element 222 in a first, "latch open," position, as seen in FIG. 13. In this position, latching tab 224 on latching element 222 is in a non-latching position relative to plate 132 of door assembly 130. In a second position, tab portion 254 of biasing element 252 is in contact with back-facing surface 222b of latch element 222, as best seen in FIG. 12. In this second position, latching tab 224 on latching element 222 is in a latching position relative to door plate 132 of door assembly 130. Door assembly 130 is held in the closed position by a latch assembly 210, as seen in FIG. 12.

A door sensor 262 is mounted on flange 62 to determine when door assembly 130 is in a closed position. Sensor 262 is preferably a magnetic sensor.

Door assembly 130 and pressure vessel 52 are each formed of a material capable of withstanding elevated temperatures and pressures.

Sterilizer 50 is dimensioned to sterilize articles contained within container 300, best seen in FIGS. 14-24. Container 300 is dimensioned to be placed within pressure vessel 52. Container 300 is comprised of a tray, that is dimensioned to hold medical instruments to be sterilized, and a lid 390, that is dimensioned to rest upon tray 310.

Figure 6:
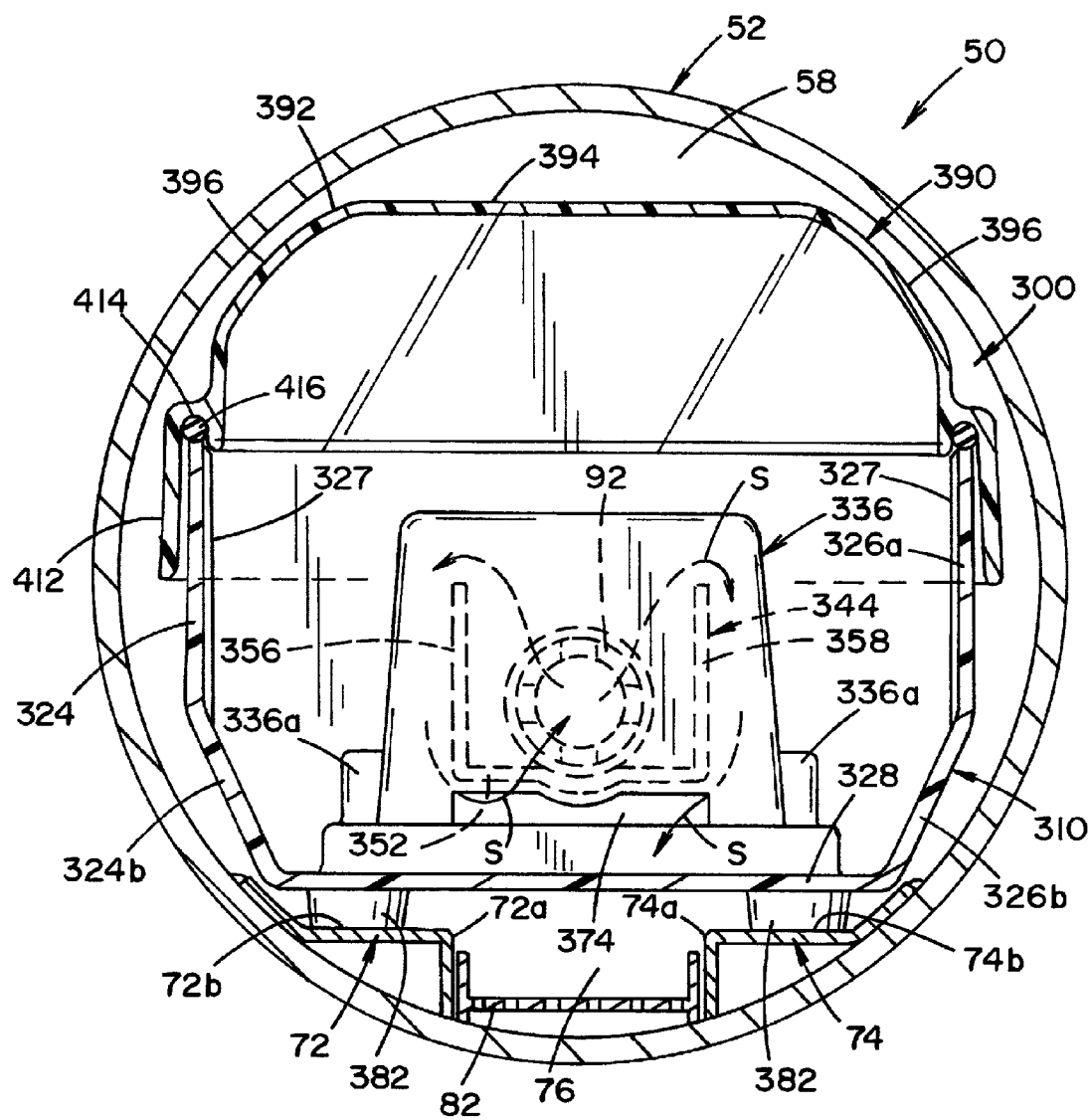
FIG. 6 is an enlarged, cross-sectional view taken along lines 6-6 of FIG. 4.
Figure 7:
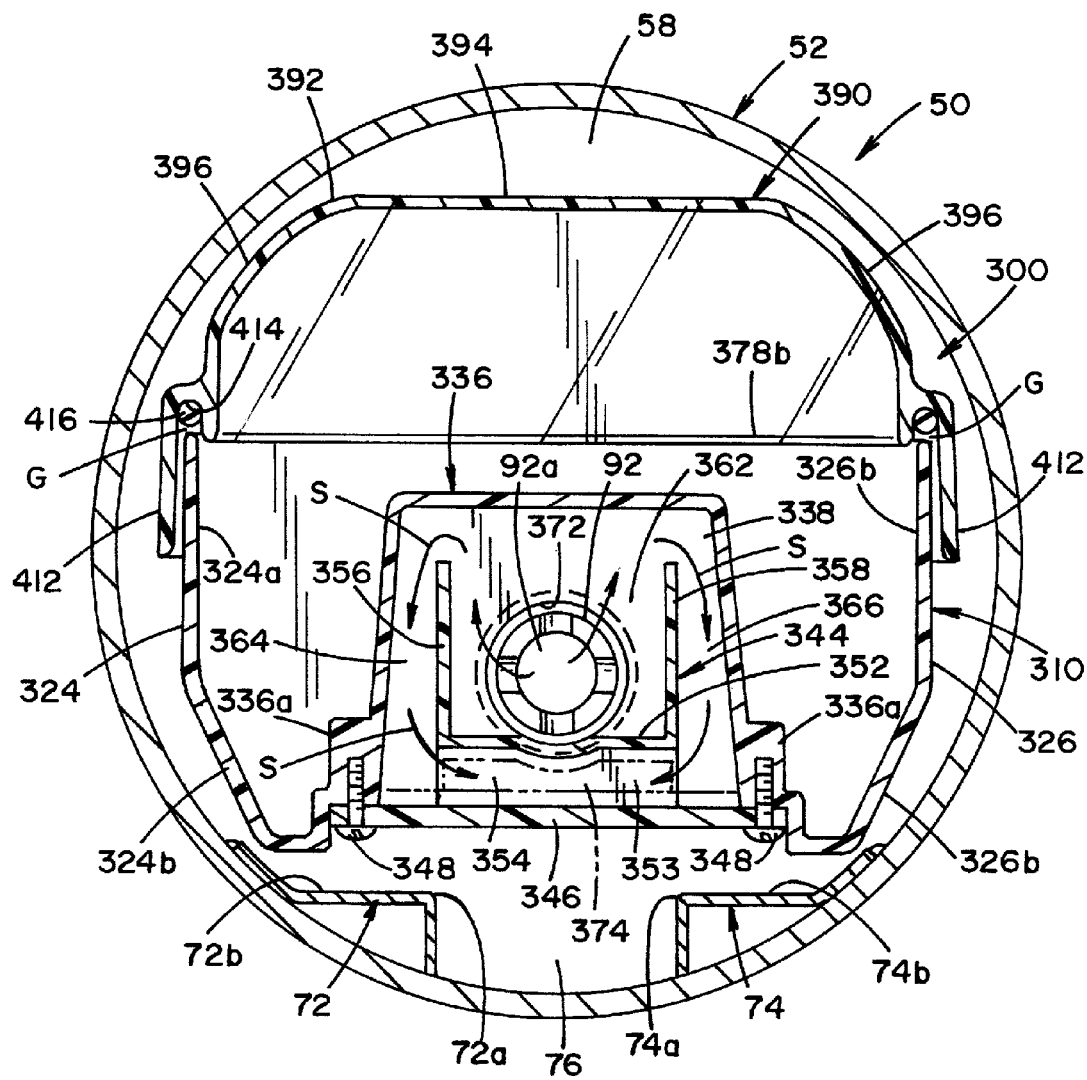
FIG. 7 is a cross-sectional view taken along lines 7-7 of FIG. 4.

Tray 310 is generally rectangular in shape and has a front end 312 and a back end 314. Front end 312 includes a generally planar, front end wall 316. A U-shaped handle 322 extends outwardly from front end wall 316 of tray 310. Spaced-apart side walls 324, 326 extend from front end wall 316 and are connected to a back end wall 318 at back end 314 of tray 310. Each side wall 324, 326 has an upper portion 324a, 326a and a lower portion 324b, 326b, respectively. Spaced-apart ribs 327 are provided along the inner surface of upper portions 324a, 326a of sidewalls 324, 326 to reinforce the same. Lower portions 324b, 326b of side walls 324, 326 slope inwardly and communicate with a flat bottom wall 328. End walls 316, 318, side walls 324, 326, and bottom wall 328 define an interior area 332 within tray 310 for receiving the medical instruments to be sterilized. A compartment or housing 336 is molded or otherwise formed at back end 314 of the tray 310. Back end wall 318 of tray 310 forms the back wall of compartment 336, as shown in FIG. 4. In the embodiment shown, compartment 336 is molded as part of tray 310. Compartment 336 is generally trapezoidal in shape, as best seen in FIGS. 6 and 7. Compartment 336 defines an inner chamber 338 that is separated from the interior area 332 of tray 310. Compartment 336 defines an opening on the bottom or underside of tray 310. An insert 344 is dimensioned to be inserted into chamber 338 defined by compartment 336 and to close the opening at the lower end of compartment 336. Insert 344 includes a base plate 346 that is dimensioned to close the opening defined at the bottom of compartment 336. Conventional fasteners 348 extending through base plate 346 into molded regions 336a of compartment 336 attach base plate 346 to compartment 336, as seen in FIG. 7. Base plate 346 supports an intermediate wall 352 that is spaced from base plate 346 by a support 354. Spaced-apart side panels 356, 358 extend upwardly from intermediate wall 352. As best seen in FIG. 7, side panels 356, 358, intermediate wall 352, and support 354 are dimensioned to be narrower than compartment 336 and, thus, define a central chamber 362 and side chambers 364, 366 within compartment 336. A cylindrical opening 372 is formed in the back end wall 318 of tray 310 and communicates with central chamber 362 within compartment 336. Opening 372 is cylindrical in shape and is dimensioned to receive connector 92 attached to pressure vessel 52, as illustrated in the drawings. A slot 374 is formed in the base of compartment 336 to connect interior area 332 within tray 310 with space 353 defined between base plate 346 and intermediate wall 352 of insert 344. As best seen in FIG. 7, space 353 communicates with side chambers 364, 366, defined between insert 344 and compartment 336. Compartment 336, thus, defines a convoluted path between opening 372 in back end wall 318 and slot 374 at the base of compartment 336 in the bottom of tray 310.

Tray 310 has an upper edge 378 that is generally rectangular in shape when viewed from above, as seen in FIG. 22. Upper edge 378 includes elevated portions 378a that extend along upper portions 324a, 326a of sidewalls 324, 326 and lower portions 378b that extend along the upper edges of front and back end walls 316, 318.

A plurality of legs 382 extends from bottom wall 328 of tray 310. In the embodiment shown, four (4) spaced-apart legs 382 are provided on tray 310. Legs 382 are spaced-apart so as to rest upon rails 72, 74 in pressure vessel 52. Angled ramps 384, best seen in FIG. 17, extend from the bottoms of legs 382 to the underside of bottom wall 328 of tray 310.

Lid 390 is generally cup-shaped and is dimensioned to mate, i.e., rest upon the upper edge 378 of tray 310. Lid 390 has a contoured top portion 392 having a flat top wall 394 and sloping side walls 396 that curve downwardly and away from flat top wall 394. A skirt or collar 412 is formed along the lower edge of the lid. Skirt or collar 412 is larger in profile than contoured portion 392 and is offset therefrom. A downward-facing, rectangular channel 414 is defined on the underside of lid 390 between contoured portion 392 and skirt 412. A continuous gasket 416 is disposed in channel 414 in lid 390. Channel 414 and gasket 416 are dimensioned to rest upon upper edge 378 of tray 310. Specifically, lid 390 is dimensioned to rest upon elevated portions 378a of sidewalls 324, 326 of tray 310. When lid 390 rests on elevated portions 378a of tray 310, a gap "G" is formed between gasket 416 and lower portions 378b along front and back end walls 316, 318 of tray 310, as best seen in FIGS. 7 and 10. Skirt portion 412 of lid 390 is dimensioned to be spaced from and to overlay and telescope over side walls 324, 326 and front and back end walls 316, 318 of tray 310 as shown in the drawings. Skirt 412 of lid 390 is dimensioned to loosely attach to tray 310.

Lid 390 is molded in such a way as to include two recesses or depressions 422 that are separated by a wall 426. Recesses or depressions 422, 424 are disposed on opposite sides of lid 390 basically to define a grip or handle 428 for removing lid 390 from tray 310. Lid 390 and tray 310 are preferably each one-piece, molded elements formed of a high-temperature polymer material.

According to one aspect of the present invention, the outer profile of container 300, i.e., tray 310 and lid 390, is dimensioned to fit closely within inner cavity 58 defined by pressure vessel 52. In this respect, a small space or gap "G" exists between lid 390 of container 300 and the inner surface of pressure vessel 52 when container 300 is disposed within sterilizer 50, as best seen in FIGS. 6 and 7.

When container 300 is positioned within pressure vessel 52, connector 92 (i.e., the steam inlet) extends through opening 372 in back end wall 318 of tray 310, wherein the end of connector 92 communicates with central chamber 362 defined by compartment 336 within tray 310. Central chamber 362 communicates with space 353 formed by insert 344 via side chambers 364, 366 defined between side panels 356, 358 of insert 344 and the side walls of compartment 336. Gap 353 communicates with the interior of the tray through slot 374 at the base of compartment 336.

In accordance with another aspect of the present invention, when tray 310 is disposed within pressure vessel 52, handle 322 of tray 310 extends into cup-shaped recess 172 of liner 142 of door assembly 130.

Referring now to the operation of sterilizer 50, one or more articles to be sterilized, such as medical, dental, pharmaceutical, veterinary or mortuary instruments, or other similar-sized devices are loaded into tray 310. A mesh tray or a silicone mat (not shown) may be placed in tray 310 to hold the instruments that are being sterilized. Lid 390 is then placed onto tray 310 and container 300 is then inserted into inner cavity 58 of pressure vessel 52 through the opening at front end 54 of sterilizer 50. Legs 382 of tray 310 rest upon and slide along flat surfaces 72b, 74b of rails 72, 74, as container 300 is inserted into pressure vessel 52. Ramps 384 on legs 382 facilitate insertion of container 300 into pressure vessel 52. Connector 92 at back end 56 of sterilizer 50 is disposed to be aligned with opening 372 in back end wall 318 of tray 310. Flange 98 on connector 92, abutting back end wall 318, acts as a stop to position container 300 within pressure vessel 52, as illustrated in FIG. 4. As seen in the drawing, the open end of connector 92 is disposed within central chamber 362 of compartment 336 when flange 98 on connector 92 abuts back end wall 318.

With container 300 fully inserted into pressure vessel 52, door assembly 130 is moved to a closed position as shown in FIGS. 3 and 5. In this respect, when door assembly 130 is in an open position (as shown in FIGS. 1 and 2), latch element 222 is in a position as shown in FIG. 13, where a back edge of latch element 222 is held in detent 256 of biasing element 252. As door assembly 130 moves from an open position to a closed position, door plate 132 engages paw 226 on latch element 222 and causes latch element 222 to move counterclockwise when viewed from above as shown in FIGS. 12 and 13, wherein the back edge of latch element 222 moves onto tab portion 254 of biasing element 252, as shown in FIG. 12, and L-shaped tab 224 of latch element 222 captures the free edge of flat section 132a of door plate 132. Biasing element 252 maintains a biasing force on latch element 222 to maintain L-shaped tab 224 in the position shown in FIG. 12.

According to one aspect of the present invention, latch element 222 is self locking. In this respect, the present invention provides a "fail-safe" mechanism when pressure is applied in the sterilization chamber. The greater the pressure within the inner cavity 58, the tighter the latch element 222 engages the door plate 132.

As best seen in FIG. 3, when door assembly 130 is in a closed position, container 300 is contained within a sterilization chamber defined by inner cavity 58 of pressure vessel 52 and recess 146 of door assembly 130. As best seen in FIG. 5, a portion (i.e., the free end) of handle 322 extends into cup-shaped recess 172 of door assembly 130.

Figure 8:
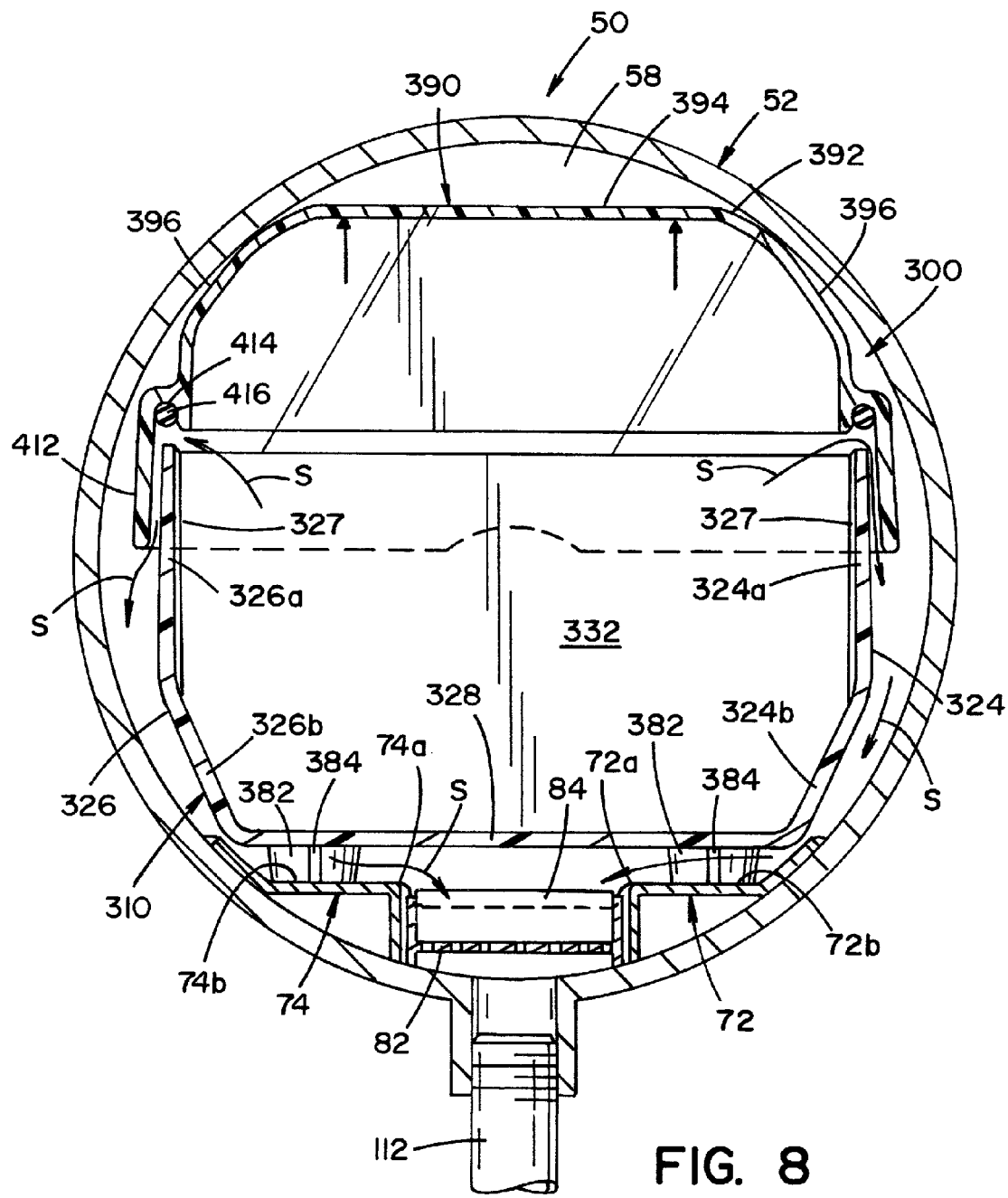
FIG. 8 is a cross-sectional view taken along lines 8-8 of FIG. 5.

Sensor 262 provides a signal to the system controller (not shown) when door assembly 130 is in a closed position. Similarly, sensor 244 provides a signal when latching element 222 is in a "door-latching" position, as shown in FIG. 12. Only when both sensors simultaneously indicate that door assembly 130 is in a closed position and latching element 222 is in a door-latching position will the controller initiate a sterilization cycle. During a sterilization cycle, steam from an external source 96 is conveyed through inlet line 94 to pressure vessel 52 and container 300. The pressurized steam is forced into central chamber 362 of compartment 336, as illustrated by arrows "S" in FIG. 7. From central chamber 362, the steam flows over side panels 356, 358 and through side chambers 362, 364 to gap 353. From gap 353, the steam flows through slot 374 into the interior of tray 310. Steam within container 300 is allowed to exit container 300 through gaps "G" defined between tray 310 and lid 390. As the steam continues to be introduced into container 300, the pressure within container 300 will increase to where the steam pressure acting upon the underside of lid 390 will force lid 390 off of tray 310, as illustrated in FIG. 8. In effect, the configuration of lid 390 relative to tray 310 allows lid 390 to lift off tray 310 and release steam from container 300 into cavity 58 of pressure vessel 52. As shown in FIG. 8, the dimensions of inner cavity 58 limits the movement of lid 390 relative to tray 310. In addition, steam is forced into back end 56 of pressure vessel 52 and to the areas within pressure vessel 52 that surround container 300 through openings 99 in connector 92, as illustrated in FIG. 4.

During a sterilization cycle, as pressure builds up within inner cavity 58 of pressure vessel 52, leg portions 152a, 152b of gasket 152 are forced outwardly against flat section 132a of door plate 132 and flange 62 of pressure vessel 52, respectively, by the pressure between leg portions 152a, 152b, thereby forming a seal between door plate 132 and flange 62.

Steam or condensate is forced out of inner cavity 58 through sterilant outlet line 112 on the underside of pressure vessel 52. By positioning outlet line 112 at the lowest point within pressure vessel 52, steam or condensate collected within pressure vessel 52 may be withdrawn from pressure vessel 52 during operation of a sterilization cycle.

After a predetermined period of time that is sufficient for the heated steam to decontaminate, i.e., sterilize, the medical instruments within container 300, the controller shuts down the flow of steam to pressure vessel 52. It is contemplated that clean, filtered air may be introduced into pressure vessel 52 to help dry the medical instruments within container 300.

Once pressure has been released inside sterilizer 50, the controller unlocks door assembly 130 to allow the door to be opened. Door assembly 130 is unlocked or unlatched by the controller, actuating actuator 246 which causes pin 246a to engage latch element 222 and pivot L-shaped tab 224 of latch element 222 away from the edge of flat section 132a of door plate 132, as illustrated in FIG. 13. Actuator 246 causes the back edge of latch element 222 to move into detent 356 of biasing element 252 which holds the latch element 222 in an unlatched position, as shown in FIG. 13. U-shaped handle 322 extends partially from inner cavity 58 of pressure vessel 52, wherein container 300 can be easily grasped and withdrawn from pressure vessel 52, as illustrated in FIG. 10.

As noted above, following a sterilization cycle, once pressure is removed from pressure vessel 52, lid 390 will settle back onto upper edge 378 of tray 310. As illustrated in the drawings, the distance lid 390 is allowed to move within pressure vessel 52 is less than the height of skirt 412 of lid 390, wherein lid 390 will never become completely separated from tray 310.

It will be appreciated that the medical instruments may be relatively hot and that condensate may accumulate within tray 310 during a steam sterilizing cycle. The presence of condensate on the instruments within tray 310 does not affect the sterilization of the instruments or the availability of the instruments for use in a surgical procedure.

The present invention thus provides a sterilizer 50 for flash sterilization of small quantities of medical instruments. The sterilization occurs in an easily handled container 300 that remains sterile following such sterilization.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A sterilizer for sterilizing medical instruments, said sterilizer comprised of:
    a pressure vessel having an opening at an open end, a closed end opposite the open end, a body defining a cavity between the open end and the closed end, a connector extending into said cavity through said closed end of said pressure vessel, and a sterilant outlet formed in said cavity, said connector being connected to a sterilant source from which pressurized sterilant is provided to said connector;
    a container configured to receive the pressurized sterilant from said connector, the container being dimensioned to fit within said pressure vessel through said open end, said container comprising a tray and a lid dimensioned to removably join to said tray to define an interior area configured to hold the medical instruments to be sterilized, said tray having an opening formed in an end wall thereof that is adjacent to said closed end of said pressure vessel and aligned with said connector when said container is placed within said pressure vessel, said opening being configured to receive said connector therein to enable said pressurized sterilant provided to said connector to be introduced into said interior area, said lid being configured to disjoin from said tray to form a gap between said lid and said tray as a result of said pressurized sterilant in said interior area acting on an underside of said lid such that said pressurized sterilant escapes from said interior area through said gap into said cavity of said pressure vessel and out of said cavity through said sterilant outlet of said pressure vessel; and
    a door assembly configured to close said opening to seal said cavity to perform said sterilizing of said medical instruments.

2. The sterilizer as defined in claim 1, wherein said pressure vessel is dimensioned to engage said lid and limit movement thereof when said lid is disjoined from said tray as a result of said pressurized sterilant in said interior area acting on the underside of said lid.

3. The sterilizer as defined in claim 1, wherein said pressurized sterilant introduced into said interior area is steam that disjoins said lid from said tray as a result of said pressurized sterilant in said interior area acting on an underside of said lid.

4. The sterilizer as defined in claim 1, wherein said pressure vessel is generally cylindrical in shape.

5. The sterilizer as defined in claim 1, wherein said container further comprises a tortuous area defined between said opening of said container and said interior area of said container through which said pressurized sterilant passes after being provided to said container by said connector.

6. The sterilizer as defined in claim 1, wherein said sterilant outlet is disposed at a lowest point in said cavity of said pressure vessel.

7. The sterilizer as defined in claim 1, wherein said door assembly includes a concave inner surface that defines a recess.

8. The sterilizer as defined in claim 7, wherein a downward-sloping surface is disposed at a lower portion of said door assembly, said downward-sloping surface being dimensioned to extend from said concave inner surface of said door assembly into said cavity of said pressure vessel when said door assembly is in a closed position.

9. The sterilizer as defined in claim 1, wherein said container further includes a handle that extends from an end of said container opposite that of said end wall of said tray, said container being dimensioned such that said handle extends out of said open end of said pressure vessel when said container is disposed within said pressure vessel.

10. The sterilizer as defined in claim 9, wherein said door assembly includes a concave inner surface that defines a recess, said handle on said container being disposed within said recess when said door assembly is in a closed position.

11. The sterilizer as defined in claim 9, wherein said handle is formed as part of said tray.

12. The sterilizer as defined in claim 11, wherein said tray is formed of a polymer material.

13. The sterilizer as defined in claim 12, wherein said lid is formed of a polymer material that is at least partially transparent.

14. The sterilizer as defined in claim 1, further comprising:
    a locking assembly for maintaining said door assembly in a closed position during a sterilization cycle.

15. The sterilizer as defined in claim 14, wherein said locking assembly includes an over-center latch, and
    wherein a holding force of said over-center latch increases as pressure within said pressure vessel increases.

16. The sterilizer as defined in claim 15, wherein said locking assembly includes a solenoid for releasing said over-center latch.

17. The sterilizer as defined in claim 1, wherein said connector is a tube extending into said cavity of said pressure vessel and into said opening of said container when said container is placed within said pressure vessel.

18. The sterilizer as defined in claim 17, wherein said tube communicates with said interior area via a convolute path defined between said opening of said container and said interior area of said container.

19. The sterilizer as defined in claim 1, wherein said lid is configured to completely disjoin from said tray.

20. A method of sterilizing medical instruments, comprising the steps of:
    providing a pressure vessel having an opening at an open end, a closed end opposite the open end, a body defining a cavity between the open end and the closed end, a connector extending into said cavity through said closed end of said pressure vessel, and a sterilant outlet formed in said cavity, said connector being connected to a sterilant source from which pressurized sterilant is provided to said connector;
    fitting a container within said pressure vessel through said open end, said container comprising a tray and a lid dimensioned to removably join to said tray to define an interior area configured to hold the medical instruments to be sterilized, said tray having an opening formed in an end wall thereof that is adjacent to said closed end of said pressure vessel and aligned with said connector to receive said connector therein to enable said pressurized sterilant provided to said connector to be introduced into said interior area when said container is placed within said pressure vessel;

providing a door assembly configured to close said opening to seal said cavity to perform said sterilizing of said medical instruments;

introducing said pressurized sterilant into said interior area of said fitted container such that said lid is disjoined from said tray to form a gap between said lid and said tray as a result of said pressurized sterilant in said interior area acting on an underside of said lid such that said pressurized sterilant escapes from said container through said gap into said cavity of said pressure vessel and out of said cavity through said sterilant outlet of said pressure vessel;

collecting said pressurized sterilant and condensate at a bottom of said open end of said pressure vessel; and maintaining said pressurized sterilant in said pressure vessel for a period of time sufficient to sterilize said medical instruments in said container.

\* \* \* \* \*